US009924652B1

(12) United States Patent
Kinkade et al.

(10) Patent No.: US 9,924,652 B1
(45) Date of Patent: Mar. 27, 2018

(54) WATERMELON POLLENIZER SP-7

(71) Applicant: Syngenta Participations AG, Basel (CH)

(72) Inventors: Matt Kinkade, Woodland, CA (US); James P. Brusca, Davis, CA (US); Dean Geoffery Liere, Gilroy, CA (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/386,360

(22) Filed: Dec. 21, 2016

(51) Int. Cl.
| | | |
|---|---|---|
| *A01H 5/08* | (2006.01) | |
| *A01H 1/02* | (2006.01) | |
| *A01H 4/00* | (2006.01) | |
| *C12N 15/82* | (2006.01) | |
| *C12N 5/04* | (2006.01) | |
| *A01G 17/02* | (2006.01) | |
| *A01C 7/00* | (2006.01) | |

(52) U.S. Cl.
CPC .................. *A01H 5/08* (2013.01); *A01C 7/00* (2013.01); *A01G 17/02* (2013.01); *A01H 1/02* (2013.01); *A01H 4/005* (2013.01); *A01H 4/008* (2013.01); *C12N 15/8241* (2013.01)

(58) Field of Classification Search
CPC ....................................................... A01H 5/08
See application file for complete search history.

(56) References Cited

U.S. PATENT DOCUMENTS

| | | | |
|---|---|---|---|
| 5,007,198 A | 4/1991 | Gray et al. | |
| 6,355,865 B1 | 3/2002 | Elmstrom | |
| 6,759,576 B2 | 7/2004 | Zhang et al. | |
| 7,071,374 B2 | 7/2006 | Zhang et al. | |
| 7,528,298 B2 | 5/2009 | Zhang et al. | |
| 7,550,652 B2 | 6/2009 | Zhang et al. | |
| 8,173,873 B2 | 5/2012 | Zhang et al. | |
| 8,212,118 B1 * | 7/2012 | Brusca ..................... | A01H 5/08 47/6 |
| 9,370,146 B1 | 6/2016 | Bernier | |
| 2003/0121075 A1 | 6/2003 | Barham | |
| 2003/0163852 A1 | 8/2003 | Barham et al. | |

FOREIGN PATENT DOCUMENTS

WO    2000070933 A1    11/2000

OTHER PUBLICATIONS

Rudich et al (Scientia Horticulturae, 5 (1976) 339-344).*
Sedgley et al (Ann. Bot. 42, 609-616, 1978).*
PVP Certificate No. 200300006, issued Sep. 12, 2003.
PVP Certificate No. 200700023, issued Jun. 3, 2009.
PVP Certificate No. 201000008, issued Jun. 22, 2010.
PVP Certificate No. 201200091, issued Jan. 18, 2013.
Buttrose et al., "Some effects of light intensity, daylength and temperature on growth of fruiting and non-fruiting watermelon (Citrullus lanatus)", Ann. Bot. 42, pp. 599-608 (1978).
Crall et al., "SSDL: A high-quality icebox watermelon breeding line resistant to fusarium wilt and anthracnose," HortScience 29(6); 707-708 (1994).
Davis et al., "Powdery mildew: An emerging disease of watermelon in the United States," Cucurbit Genetics Cooperative Report 24:42-48 (2001).
Davis et al., "Watermelon resistance to powdery mildew race 1 and race 2," Cucurbitaceae 2006, Holmes, ed. Universal Press, Raleigh, NC pp. 412-420.
Davis et al., "Evaluation of watermelon and related species for resistance to race 1W powdery mildew," J. Amer. Soc. Hort. Sci. 132(6): 790-795 (2007).
Guner et al., "Gene List for Watermelon," Dept. of Horticultural Science, NC State University, Raleigh, NC (2014).
Gusmini et al., "Foundations of yield improvement in watermelon," Crop Science 45: 141-146 (2005).
Hegde et al., "Physiological analysis of growth and yield of watermelon (Citrullus lanatus Thunb Musf) in relation to irrigation and nitrogen fertilization," J. Agronomy & Crop Science, 160: 296-302 (1988).
Hochmuth et al., "Cultural Management" in watermelons: Characteristics, Production, and Marketing (Virginia, ASHS Press, 2001), pp. 78-97.
Yasutaka Kano, "Effects of summer day-time temperature on sugar content in several portions of watermelon fruit (Citrullus lanatus)," J. Hort. Science & Biotechnology, 79(1): 142-145 (2004).
Karchi et al., "Alena watermelon-A quality cultivar for export and local markets," Cucurbit Genetics Cooperative Report: 6 pp. 59-61 (1983).
Karchi et al., "The importance of cultural practices in materializing yield potential in a tetraploid watermelon cultivar," Cucurbit Genetics Coooperative Crop Genetics Cooperatives 6: 59-61 Article 30 (1983).
Kenny et al., "Relative rind toughness among watermelon varieties," American Society for Horticultural Science: 38, pp. 537-540 (1941).
Maynard et al., "Triploid watermelon production practices and varieties," Acta Horticulture 318: pp. 169-178 (1992).
Nerson et al., "Harvesting watermelons before ripening impairs their quality," Agricultural Research Organization, Series 5, No. 1090 (1981).
NeSmith et al., "Fruit set of triploid watermelons as a function of distance from a diploid pollinizer," HortScience 36(1): 60-61 (2001).

(Continued)

*Primary Examiner* — Lee A Visone
(74) *Attorney, Agent, or Firm* — Karen A. Magri

(57) ABSTRACT

The present invention provides novel watermelon cultivar SP-7 and plant parts, seed, and tissue culture therefrom. The invention also provides methods for producing a watermelon plant by crossing the watermelon plants of the invention with themselves or another watermelon plant. The invention also provides watermelon plants produced from such a crossing as well as plant parts, seed, and tissue culture therefrom. Further provided are methods of producing triploid watermelon seed and plants and seedless watermelon fruit produced therefrom as well as the triploid watermelon seed and plants and the seedless fruits produced by such methods.

27 Claims, 3 Drawing Sheets

(56) References Cited

OTHER PUBLICATIONS

Poehlman et al., "Quantitative Inheritance," Breeding Field Crops, 4th Ed., Iowa State University Press, Ames, p. 71 (1995).
C.F. Poole, "Genetics of Cultivated Cucurbits," The Journal of Hereditary: 35, pp. 122-128 (1944).
D. R. Porter, "Inheritance of certain fruit and seed characters in watermelons," Hilgardia, vol. 10, No. 12 pp. 489-509 (1937).
Rhodes et al., "Gene List for Watermelon," Cucurbit Genetics Cooperative Report 22: 61-77 (Article 23) (1999).
Scott et al., "Calcium fertilization and cultivar affect watermelon rind thickness and resiliency," HortScience, vol. 25(9), p. 1075 (1990).
Sundstrom et al., "Influence of K and Ca on quality and yield of watermelon," J. Amer. Soc. Hort. Sci., 108(5): 879-881 (1983).
Susin et al., "Fertility and pollen tube growth in polyploid melons (*Cucumis melo* L.)," Euphytica 93: pp. 369-373 (1997).
Thomas et al., "Evaluatio of U.S. plant introductions of watermelon for resistance to powdery mildew," HortScience 40(1): pp. 154-156 (2005).
Wolf et al., "Genetic variability in flower attractiveness to honeybees (*Apis mellifera* L.) within the genus *Citrullus*," HortScience 34(5): 860-863 (1999).
Min et al., "Identification of quantitative trait loci associated with fruit traits in watermelon and analysis of their genetic effects," Acta Genetica Sinica 27(10): 902-910 (2000).
Suigiyama et al., "Rind hardness of watermelons and the structures of rind tissues and cells," Journal of the Japanese Society for Horticultural Science 68(1): 108-116 (1999).
U.S. Appl. No. 62/437,187, filed Dec. 21, 2016, entitled "Prolific Flowering Watermelon,".

\* cited by examiner

WATERMELON POLLENIZER SP-7

FIELD OF THE INVENTION

This invention is in the field of watermelon plants, in particular, the invention relates to a novel watermelon pollenizer, which can be used to pollinate triploid watermelon plants for production of seedless watermelon fruit.

BACKGROUND OF THE INVENTION

This invention relates to a new and unique watermelon variety, designated SP-7.

Watermelon is an important horticultural crop that accounts for 2% of the world area devoted to vegetable crops. There were 3,810,535 hectares (Ha) of watermelon grown in the world, and 51,110 Ha of watermelons grown in the United States in 2009. Asia is by far the most important watermelon production site with 78% of the world area and 83.4% of the world production of 100,687,056 metric tons. The estimated annual world watermelon value exceeded $7.6 billion when using the United States average price for 1995-1997. Watermelon is grown in at least forty-four states in the United States, with Florida, Georgia, California, and Texas, having long warm growing seasons, being the major producing states. In the United States, watermelon production has increased from 1.2 M tons in 1980 to 3.8 M tons in 2009, with an annual farm value of $470 million (U. S. Department of Agriculture, Agricultural Statistics, 2009).

In recent years, there has been an increase in consumer demand for seedless watermelons, and production of seedless watermelon has increased significantly. Triploid seedless watermelons have been commercially grown in the United States since the late 1980's. Currently, over 80% of the watermelons produced in the United States are triploid seedless watermelons. Seedless watermelon receives well above the average price for seeded watermelons in the market. Triploid seedless watermelon also produces higher yields than the diploid seeded watermelons.

Triploid seedless watermelon is a true F1 hybrid between a tetraploid watermelon, as the female parent, and a diploid watermelon, as the male parent (Kihara, H. 1951, *Triploid Watermelons*, Proceedings of American Society for Horticultural Science, 58:217-230). Diploid watermelons have 22 chromosomes (2N=2X=22) in their somatic cells, and tetraploid watermelons have 44 chromosomes (2N=4X=44) in their somatic cells. Cells with three sets of homologous chromosomes are said to be triploid and are designated as 3X. When female flowers of tetraploid plants are cross pollinated by the male flowers of diploid plants, the fruits produced by the tetraploid plants contain triploid seeds that produce triploid plants. The triploid seedless watermelons have 33 chromosomes (2N=3X=33) in their somatic cells. When the triploid plants are grown with diploid plants in the same field, the triploid plants produce fruits that are seedless. The seedless condition in triploid watermelon is the result of the presence of three homologous sets of chromosome per somatic cell rather than the usual two. The inability of the triploid zygote to produce normal viable gametes (pollen and egg cells) causes the absence of seeds in triploid fruits. Typically, seedless watermelons contain small edible white ovules, similar to those in immature cucumbers.

Watermelon, in general, and seedless watermelon in particular, is an important and valuable vegetable crop. Thus, there is an ongoing need for improved watermelon pollenizer varieties for production of seedless watermelon fruit.

SUMMARY OF THE INVENTION

According to the invention, there is provided a novel watermelon pollenizer variety, designated SP-7, characterized by small (e.g., in the range of about 1 to 3.5 kg), round fruits with a light green (Charleston Gray) skin color, brittle rind and yellow flesh; a dark brown mottled seed color; thin (lacy) vines; small leaves with deep lobes; and resistances to Anthracnose Race 1, *Fusarium* Wilt Races 1 and 2, and Powdery Mildew Race 1. SP-7 is further characterized by earlier presentation of male flowers and production of larger male flowers, with more male flowers at peak flowering time, as compared with SP-6.

The invention also encompasses the seeds of watermelon cultivar SP-7, the plants of watermelon cultivar SP-7, plant parts of the watermelon cultivar SP-7 (including fruit, seed, gametes, rootstock, shoots), methods of producing seed from watermelon cultivar SP-7, and methods for producing a watermelon plant by crossing the watermelon cultivar SP-7 with itself or another watermelon plant, methods for producing a watermelon plant containing in its genetic material one or more transgenes, and the transgenic watermelon plants produced by that method. The invention also relates to methods for producing other watermelon plants derived from watermelon cultivar SP-7 and to watermelon plants, parts thereof and seed produced by the use of those methods. The present invention further relates to hybrid watermelon seeds and plants (and parts thereof including fruit) produced by crossing watermelon cultivar SP-7 with another watermelon plant, e.g., hybrid triploid seeds produced by crossing with a tetraploid watermelon plant and diploid plants produced by crossing SP-7 with another diploid plant. The invention further relates to methods of producing triploid, seedless watermelon fruit by crossing watermelon cultivar SP-7 as a pollenizer with a female triploid line, and to the seedless watermelon fruits so produced.

The invention further contemplates grafted watermelon plants and methods of producing a grafted watermelon plant, where watermelon variety SP-7 can be used as either the rootstock or the scion.

In another aspect, the present invention provides regenerable cells for use in tissue culture of watermelon line SP-7. In embodiments, the tissue culture is capable of regenerating plants having all or essentially all of the physiological and morphological characteristics of the foregoing watermelon plant and/or of regenerating plants having the same or substantially the same genotype as the foregoing watermelon plant. In embodiments, the regenerated plant is a diploid plant. In exemplary embodiments, the regenerable cells in such tissue cultures are meristematic cells, cotyledons, hypocotyl, leaves, pollen, embryos, roots, root tips, anthers, pistils, ovules, shoots, stems, petiole, pith, flowers, capsules and/or seeds as well as callus and/or protoplasts derived from any of the foregoing. Still further, the present invention provides watermelon plants regenerated from the tissue cultures of the invention.

As a further aspect, the invention provides a method of producing watermelon seed, the method comprising crossing a plant of watermelon cultivar SP-7 with itself or a second watermelon plant (e.g., a diploid or tetraploid plant) and allowing seed to form (e.g., diploid or triploid hybrid seed, respectively). Optionally, the method further comprises collecting the seed.

Another aspect of the invention provides methods for producing hybrids and other watermelon plants derived from watermelon cultivar SP-7. Watermelon plants derived by the use of these methods are also part of the invention as well as plant parts, seed, gametes and tissue culture from such hybrid or derived watermelon plants.

In representative embodiments, a watermelon plant derived from watermelon cultivar SP-7 comprises cells comprising at least one set of chromosomes derived from watermelon cultivar SP-7. In embodiments, the derived watermelon plant is a diploid plant. In embodiments, the derived watermelon plant is a triploid plant. In embodiments, the derived watermelon plant is a tetraploid plant.

In embodiments, a watermelon plant or population of watermelon plants derived from watermelon cultivar SP-7 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., theoretical allelic content; TAC) from watermelon line SP-7, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line SP-7, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology. In embodiments, the derived watermelon plant is a diploid plant. In embodiments, the derived watermelon plant is a triploid plant. In embodiments, the derived watermelon plant is a tetraploid plant. In embodiments, the watermelon plant derived from watermelon cultivar SP-7 is one, two, three, four, five or more breeding crosses removed from watermelon cultivar SP-7.

In embodiments, a hybrid or derived plant from watermelon cultivar SP-7 comprises a desired added trait(s). In representative embodiments, a watermelon plant derived from watermelon line SP-7 comprises all of the morphological and physiological characteristics of watermelon cultivar SP-7 (e.g., as described in Table 1 and shown in FIGS. 1-3), with the addition of the desired added trait(s). In embodiments, the watermelon plant derived from watermelon cultivar SP-7 comprises essentially all of the morphological and physiological characteristics of watermelon line SP-7 (e.g., as described in Table 1 and FIGS. 1-3), with the addition of a desired added trait(s). In embodiments, the plant derived from cultivar SP-7 is a diploid plant. In embodiments, the plant derived from cultivar SP-7 is a triploid plant. In embodiments, the plant derived from cultivar SP-7 is a tetraploid plant.

The invention also relates to methods for producing a watermelon plant comprising in its genetic material one or more transgenes and to the transgenic watermelon plant produced by those methods (and progeny watermelon plants comprising the transgene). Also provided are plant parts, seed and tissue culture from such transgenic watermelon plants, optionally wherein one or more cells in the plant part, seed, or tissue culture comprises the transgene. The transgene can be introduced via plant transformation and/or breeding techniques.

In another aspect, the present invention provides for single gene converted plants of watermelon cultivar SP-7. Plant parts, seed, and tissue culture from such single gene converted plants are also contemplated by the present invention. The single transferred gene may be a dominant or recessive allele. In representative embodiments, the single transferred gene confers such traits as male sterility, herbicide resistance, pest resistance (e.g., insect and/or nematode resistance), modified fatty acid metabolism, modified carbohydrate metabolism, disease resistance (e.g., for bacterial, fungal and/or viral disease), male fertility, enhanced nutritional quality, improved appearance (e.g., color), improved salt tolerance, industrial usage, or any combination thereof. The single gene may be a naturally occurring watermelon gene or a transgene introduced into watermelon through genetic engineering techniques.

The invention further provides methods for developing watermelon plants (e.g., diploid, triploid or tetraploid) in a watermelon plant breeding program using plant breeding techniques including, for example, recurrent selection, backcrossing, pedigree breeding, double haploid techniques, restriction fragment length polymorphism enhanced selection, genetic marker enhanced selection and/or transformation. Seeds, watermelon plants, and parts thereof, produced by such breeding methods are also part of the invention.

The invention also provides methods of multiplication or propagation of watermelon plants of the invention, which can be accomplished using any method known in the art, for example, via vegetative propagation and/or seed.

The invention also contemplates methods of producing triploid seedless watermelon fruits by pollinating a triploid watermelon plant with diploid pollenizer SP-7 to produce triploid seedless watermelon fruits. The invention further provides the triploid, seedless watermelon fruits.

Additional aspects of the invention include harvested products and processed products from the watermelon plants of the invention. A harvested product can be a whole plant or any plant part, as described herein. Thus, in some embodiments, a non-limiting example of a harvested product includes a seed, a fruit (e.g., including the flesh and/or rind), a rootstock and/or a shoot.

In representative embodiments, a processed product includes, but is not limited to: cut, sliced, ground, pureed, dried, canned, jarred, washed, packaged, frozen and/or heated fruit (including the fruit flesh and/or rind) of the watermelon plants of the invention, or any other part thereof. In embodiments, a processed product includes a sugar or other carbohydrate, fiber, protein and/or aromatic compound that is extracted, purified or isolated from a watermelon plant of the invention. In embodiments, the processed product includes washed and sliced fruit (or parts thereof, e.g., the fruit flesh with or without the rind) of the invention.

The seed of the invention can optionally be provided as an essentially homogenous population of seed of a single plant or cultivar. Essentially homogenous populations of seed are generally free from substantial numbers of other seed, e.g., at least about 90%, 95%, 96%, 97%, 98% or 99% pure.

In representative embodiments, the invention provides a seed of watermelon cultivar SP-7.

As a further aspect, the invention provides a plant of watermelon cultivar SP-7.

As an additional aspect, the invention provides a watermelon plant, or a part thereof, having all or essentially all of the physiological and morphological characteristics of a plant of watermelon cultivar SP-7. Optionally, the plant having all or essentially all of the physiological and morphological characteristics of a plant of watermelon line SP-7 is a diploid plant.

The invention further provides triploid, seedless watermelon fruit produced by crossing watermelon line SP-7 as the male parent with a triploid watermelon plant as the female parent.

As another aspect, the invention provides fruit and/or seed of the watermelon plants of the invention and a processed product from the fruit and/or seed of the inventive watermelon plants.

As still another aspect, the invention provides a method of producing watermelon seed, the method comprising crossing a watermelon plant of the invention with itself or a second watermelon plant (where the second watermelon plant can be a diploid or tetraploid plant). In embodiments, the method is practiced to produce seed of line SP-7 (e.g., seed increase). The invention also provides seed produced by this method and plants, and parts thereof including fruit, produced by growing the seed.

As yet a further aspect, the invention provides a method for producing a seed (e.g., a diploid seed) of a watermelon plant derived from watermelon cultivar SP-7, the method comprising: (a) crossing a watermelon plant of watermelon cultivar SP-7 with a second watermelon plant, which can optionally be a diploid plant; and (b) allowing seed of a watermelon plant derived from watermelon cultivar SP-7 to form. In embodiments, the method further comprises: (c) growing a plant from the seed derived from watermelon cultivar SP-7 of step (b); (d) selfing the plant of step (c) or crossing it to a second watermelon plant (e.g., a diploid watermelon plant) to form additional watermelon seed derived from watermelon cultivar SP-7, and (e) optionally repeating steps (c) and (d) one or more times to generate further derived watermelon seed from watermelon cultivar SP-7, wherein in step (c) a plant is grown from the additional watermelon seed of step (d) in place of growing a plant from the seed of step (b). In embodiments, the method comprises: (e) repeating steps (c) and (d) one or more times (e.g., one to three, one to five, one to six, one to seven, one to ten, three to five, three to six, three to seven, three to eight or three to ten times) to generate further derived watermelon seed. As another option, the method can comprise collecting the seed. The invention also provides seed produced by these methods and watermelon plants (e.g., diploid watermelon plants) produced by growing the seed.

Still further, as another aspect, the invention provides a method of vegetatively propagating a plant of watermelon line SP-7, e.g., via shoot proliferation and then rooting in tissue culture. Detailed methods are described by Zhang et al. (Zhang, X. P., B. B. Rhodes, H. T. Skorupska, W. C. Bridges. 1995. Generating Tetraploid Watermelon Using Colchicine in Vitro. G. Lester & J. Dunlap et al. (eds.), Cucurbitaceae '94: 134-139). In a non-limiting example, the method comprises: (a) collecting tissue capable of being propagated from a plant of watermelon line SP-7; (b) cultivating the tissue to obtain proliferated shoots; and (c) rooting the proliferated shoots to obtain rooted plantlets. Optionally, the invention further comprises growing plants from the rooted plantlets. The invention also encompasses the plantlets and plants produced by these methods, as well as seed and fruits produced therefrom.

As a further aspect, the invention provides a method of producing a grafted watermelon plant, wherein cultivar SP-7 is used as either the rootstock or the scion.

As an additional aspect, the invention provides a method of introducing a desired added trait into watermelon cultivar SP-7, the method comprising: (a) crossing a first plant of watermelon cultivar SP-7 with a second watermelon plant (e.g., a diploid plant) that comprises a desired trait to produce $F_1$ progeny; (b) selecting an $F_1$ progeny that comprises the desired trait; (c) crossing the selected $F_1$ progeny with watermelon line SP-7 to produce backcross progeny; and (d) selecting backcross progeny comprising the desired trait to produce a plant derived from watermelon cultivar SP-7 comprising a desired trait.

In embodiments, the selected progeny produces a small fruit. In embodiments, the selected progeny produces a round fruit. In embodiments, the selected progeny produces a fruit having a light green (Charleston Gray) skin. In embodiments, the selected progeny produces a fruit with a brittle rind. In embodiments, the selected progeny produces a fruit with a yellow flesh. In embodiments, the seed of the selected progeny has a dark brown mottled color. In embodiments, the selected progeny has thin (lacy) vines. In embodiments, the selected progeny produces small, deeply lobed leaves. In embodiments, the selected progeny has one or more of the following resistances, in any combination: resistance to Anthracnose Race 1, resistance to *Fusarium* Wilt Races 1 and 2, and resistance to Powdery Mildew Race 1. In embodiments, the selected progeny is characterized by earlier presentation of male flowers, production of larger male flowers and/or production of more male flowers at peak flowering time as compared with watermelon cultivar SP-6. In embodiments, the selected progeny comprises all or essentially all the morphological and physiological characteristics of watermelon line SP-7 (e.g., a described in Table 1 and FIGS. 1-3). Optionally, the method further comprises: (e) repeating steps (c) and (d) one or more times (e.g., one to three, one to five, one to six, one to seven, one to ten, three to five, three to six, three to seven, three to eight or three to ten times) to produce a plant derived from watermelon cultivar SP-7 comprising the desired trait, wherein in step (c) the selected backcross progeny produced in step (d) is used in place of the selected F1 progeny of step (b). In embodiments, the plant derived from cultivar SP-7 and comprising the desired added trait is a diploid plant. In embodiments, the plant derived from cultivar SP-7 and comprising the desired added trait is a diploid plant. In embodiments, the plant derived from cultivar SP-7 and comprising the desired added trait is a triploid plant. In embodiments, the plant derived from cultivar SP-7 and comprising the desired added trait is a tetraploid plant.

In representative embodiments, the invention also provides a method of producing a plant of watermelon cultivar SP-7 comprising a desired added trait, the method comprising introducing a transgene conferring the desired trait into a plant of watermelon cultivar SP-7. The transgene can be introduced by transformation methods (e.g., genetic engineering) or breeding techniques. In embodiments, the plant comprising the transgene produces a small fruit. In embodiments, the plant comprising the transgene produces a round fruit. In embodiments, the plant comprising the transgene produces a fruit having a light green (Charleston Gray) skin. In embodiments, the plant comprising the transgene produces a fruit with a brittle rind. In embodiments, the plant comprising the transgene produces a fruit with a yellow flesh. In embodiments, the seed of the plant comprising the transgene has a dark brown mottled color. In embodiments, the plant comprising the transgene has thin (lacy) vines. In embodiments, the plant comprising the transgene produces small, deeply lobed leaves. In embodiments, the plant comprising the transgene has one or more of the following resistances, in any combination: resistance to Anthracnose Race 1, resistance to *Fusarium* Wilt Races 1 and 2, and resistance to Powdery Mildew Race 1. In embodiments, the plant comprising the transgene is characterized by earlier presentation of male flowers, production of larger male flowers and/or production of more male flowers at peak flowering time as compared with watermelon cultivar SP-6. In embodiments, the plant comprising the transgene comprises all or essentially all of the morphological and physiological characteristics of watermelon cultivar SP-7 (e.g., as described in Table 1 and FIGS. 1-3).

The invention also provides watermelon plants (e.g., a diploid watermelon plant) produced by the methods of the invention, wherein the watermelon plant has the desired added trait as well as seed and fruits from such watermelon plants. The invention also provides seed that produces the plants derived from cultivar SP-7 and comprising a desired added trait.

According to the foregoing methods, the desired added trait can be any suitable trait known in the art including, for example, male sterility, male fertility, herbicide resistance, insect or pest (e.g., insect and/or nematode) resistance, modified fatty acid metabolism, modified carbohydrate metabolism, disease resistance (e.g., for bacterial, fungal and/or viral disease), enhanced nutritional quality, increased sweetness, increased flavor, improved ripening control, improved salt tolerance, industrial usage, or any combination thereof.

In representative embodiments, a transgene conferring herbicide resistance confers resistance to glyphosate, sulfonylurea, imidazolinone, dicamba, glufosinate, phenoxy proprionic acid, L-phosphinothricin, cyclohexone, cyclohexanedione, triazine, benzonitrile, or any combination thereof.

In representative embodiments, a transgene conferring pest resistance (e.g., insect and/or nematode resistance) encodes a *Bacillus thuringiensis* endotoxin.

In representative embodiments, transgenic plants, transformed plants (e.g., using genetic engineering techniques), single gene converted plants, hybrid plants and watermelon plants derived from watermelon cultivar SP-7 are characterized by, e.g., one or more of small fruit, round fruit, a fruit with a light green (Charleston Gray) skin color, a fruit with a brittle rind, a fruit with yellow flesh; a dark brown mottled seed color, thin (lacy) vines, small leaves with deep lobes, one or more of the disease resistances of SP-7 (e.g., resistance to Anthracnose Race 1, resistance to *Fusarium* Wilt Races 1 and 2 and/or resistance to Powdery Mildew Race 1), earlier presentation of male flowers as compared with cultivar SP-6, production of larger male flowers as compared with cultivar SP-6 and/or production of more male flowers at peak flowering time as compared with SP-6, in any combination. In representative embodiments, transgenic plants, transformed plants, hybrid plants and watermelon plants derived from watermelon cultivar SP-7 have at least 3, 4, 5, 6, 7, 8, 9, 10 or more of the morphological and physiological characteristics of watermelon cultivar SP-7 (for example, as described in the preceding sentence, and as described in Table 1 and FIGS. 1-3), or even all of the morphological and physiological characteristics of watermelon line SP-7, so that said plants are not significantly different for said traits than watermelon cultivar SP-7, as determined at the 5% significance level when grown in the same environmental conditions; optionally, with the presence of one or more desired additional traits (e.g., male sterility, disease resistance, pest or insect resistance, herbicide resistance, and the like).

In one embodiment, the present invention discloses a method for producing triploid, seedless watermelon fruit comprising the steps of interplanting watermelon variety SP-7 and triploid watermelon plants, e.g., in a field or a greenhouse; and allowing pollination of said triploid watermelon plants by pollen of said plant of watermelon variety SP-7 to obtain triploid, seedless watermelon fruit. In one embodiment, the method further comprises harvesting seedless watermelon fruit from the triploid plant.

The step of "interplanting" the diploid pollenizer and triploid plants can comprise: (i) planting seed of both pollenizer SP-7 and the triploid plant to produce the plants; (ii) planting transplants (e.g., young plants) of both pollenizer SP-7 and the triploid plant; (iii) planting seed of pollenizer SP-7 and transplants of the triploid plant; or (iv) planting transplants of pollenizer SP-7 and seed of the triploid plants.

The present invention also provides a method for interplanting plants of watermelon variety SP-7 amongst triploid watermelon plants, e.g., in a field or a greenhouse. The invention also provides a method of increasing the yield of triploid seedless watermelon plants by plants of watermelon variety SP-7, wherein the fruit are not harvested for human consumption.

In one embodiment, the present invention discloses a method of producing seeds of watermelon variety SP-7 comprising growing a plant of watermelon variety SP-7; allowing pollination of said plants, for example, open-pollination of said plants in an isolated plot or field; and harvesting seeds from said plants. In one embodiment, the method further comprises washing and drying said seed.

As a further aspect, the invention provides a method of producing triploid, seedless watermelon fruit, the method comprising: (a) crossing a watermelon plant of cultivar SP-7 as the pollenizer with a triploid watermelon plant as the female; (b) allowing triploid, seedless fruits to form on the triploid watermelon plant; and (c) optionally, harvesting the resultant triploid watermelon fruit. Also provided is a seedless watermelon fruit produced by the foregoing method.

The invention further provides a method of developing a watermelon variety (e.g., a diploid watermelon variety) in a watermelon plant breeding program using plant breeding techniques, which include employing a watermelon plant, or a part thereof, as a source of plant breeding material, the method comprising: (a) obtaining the watermelon plant, or a part thereof, of cultivar SP-7 as a source of breeding material; and (b) applying plant breeding techniques.

The invention also encompasses plant parts, plant material, pollen, ovules, leaves, fruit and seed from the watermelon plants of the invention. The invention also provides seed that produces the watermelon plants of the invention. Also provided is a tissue culture of regenerable cells from the watermelon plants of the invention, where optionally, the regenerable cells are: (a) embryos, meristem, leaves, pollen, cotyledons, hypocotyls, roots, root tips, anthers, flowers, pistils, ovules, seed, shoots, stems, stalks, petioles, pith and/or capsules; or (b) callus or protoplasts derived from the cells of (a). Further provided are watermelon plants regenerated from a tissue culture of the invention.

In still yet another aspect, the invention provides a method of determining a genetic characteristic of watermelon cultivar SP-7 or a progeny thereof, e.g., a method of determining a genotype of watermelon cultivar SP-7 or a progeny thereof using molecular genetic techniques. In embodiments, the method comprises detecting in the genome of a SP-7 plant, or a progeny plant thereof, at least a first polymorphism, e.g., comprises nucleic acid amplification and/or nucleic acid sequencing. To illustrate, in embodiments, the method comprises obtaining a sample of nucleic acids from the plant and detecting at least a first polymorphism in the nucleic acid sample (e.g., using one or more molecular markers). Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

In addition to the exemplary aspects and embodiments described above, the invention is described in more detail in the description of the invention set forth below.

DETAILED DESCRIPTION OF THE INVENTION

Figure 1:
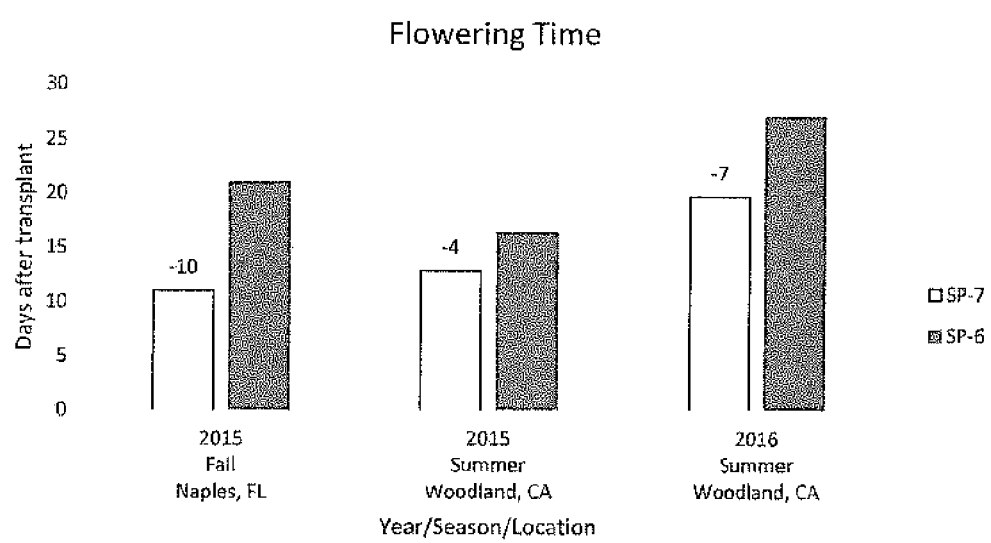
FIG. 1 shows flowering time for SP-7 (left bars) and SP-6 (right bars) as recorded in multiple field trials. Flowering time was measured as the number of days after transplant when 50% of the plants in each plot presented open male flowers. The relative difference in flowering time (in days) for SP-7 as compared with SP-6 is indicated above the bars on the left.

The present invention is based, in part, on the development of a novel watermelon pollenizer variety characterized by small (e.g., in the range of about 1 to 3.5 kg), round fruits with a light green (Charleston Gray) skin color, brittle rind and yellow flesh; a dark brown mottled seed color, thin (lacy) vines, small leaves with deep lobes, and resistances to Anthracnose Race 1, *Fusarium* Wilt Races 1 and 2, and Powdery Mildew Race 1. SP-7 is further characterized by earlier presentation of male flowers and production of larger male flowers, with more male flowers at peak flowering time, as compared with SP-6. In embodiments of the invention, a brittle rind of a watermelon fruit breaks under a pressure in the range of about 800 g to about 1,500 g when a Wagner Fruit Test™ FT11 with a 2 mm tip is used.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless the context indicates otherwise, it is specifically intended that the various features and embodiments of the invention described herein can be used in any combination.

Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Definitions

In the description and tables that follow, a number of terms are used. In order to provide a clear and consistent understanding of the specification and claims, including the scope to be given such terms, the following definitions are provided:

As used in the description of the invention and the appended claims, the singular forms "a," "an" and "the" are intended to include the plural forms as well, unless the context clearly indicates otherwise.

As used herein, "and/or" refers to and encompasses any and all possible combinations of one or more of the associated listed items, as well as the lack of combinations when interpreted in the alternative ("or").

The term "about," as used herein when referring to a measurable value such as a dosage or time period and the like, is meant to encompass variations of ±20%, ±10%, ±5%, ±1%, ±0.5%, or even ±0.1% of the specified amount.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP §2111.03. Thus, the term "consisting essentially of" when used in a claim or the description of this invention is not intended to be interpreted to be equivalent to "comprising."

"Allele". An allele is any of one or more alternative forms of a gene, all of which relate to a trait or characteristic. In a diploid cell or organism, the two alleles of a given gene occupy corresponding loci on a pair of homologous chromosomes.

"Backcrossing". Backcrossing is a process in which a breeder repeatedly crosses hybrid progeny back to one of the parents, for example, a first generation hybrid $F_1$ with one of the parental genotype of the $F_1$ hybrid.

"Cotyledon". One of the first leaves of the embryo of a seed plant; typically one or more in monocotyledons, two in dicotyledons, and two or more in gymnosperms.

"Double haploid line". A stable inbred line achieved by doubling the chromosomes of a haploid line, e.g., from anther culture. For example, some pollen grains (haploid) cultivated under specific conditions develop plantlets containing 1 n chromosomes. The chromosomes in these plantlets are then induced to "double" (e.g., using chemical means) resulting in cells containing 2n chromosomes. The progeny of these plantlets are termed "double haploid" and are essentially not segregating any more (e.g., are stable). The term "double haploid" is used interchangeably herein with "dihaploid."

"Essentially all the physiological and morphological characteristics". A plant having "essentially all the physiological and morphological characteristics" means a plant having the physiological and morphological characteristics of the recurrent parent, except for the characteristics derived from the converted gene(s).

"First water date". The date the seed first receives adequate moisture to germinate. This can and often does equal the planting date.

"Gene". As used herein, "gene" refers to a segment of nucleic acid comprising an open reading frame. A gene can be introduced into a genome of a species, whether from a different species or from the same species, using transformation or various breeding methods.

"Inbred line": As used herein, the phrase "inbred line" refers to a genetically homozygous or nearly homozygous population. An inbred line, for example, can be derived through several cycles of sib crossing and/or selfing and/or via double haploid production. In some embodiments, inbred lines breed true for one or more traits of interest. An "inbred plant" or "inbred progeny" is an individual sampled from an inbred line.

"Plant." As used herein, the term "plant" includes plant cells, plant protoplasts, plant cell tissue cultures from which plants can be regenerated, plant calli, plant clumps, and plant cells that are intact in plants or parts of plants, such as leaves, pollen, embryos, cotyledons, hypocotyl, roots, root tips, anthers, pistils, flowers, ovules, seeds, fruit, stems, and the like.

"Plant material". The terms "plant material" and "material obtainable from a plant" are used interchangeably herein and refer to any plant material obtainable from a plant including without limitation, leaves, stems, roots, flowers or flower parts, fruits, pollen, ovules, zygotes, seeds, cuttings, cell or tissue cultures, or any other part or product of the plant.

"Plant part". As used herein, a "plant part" includes any part, organ, tissue or cell of a plant including without limitation an embryo, meristem, leaf, pollen, cotyledon, hypocotyl, root, root tip, anther, flower, flower bud, pistil, ovule, seed, shoot, stem, stalk, petiole, pith, capsule, a scion, a rootstock and/or a fruit including callus and protoplasts derived from any of the foregoing. In representative embodiments, the plant part is a non-propagating plant part, for example, is not a seed.

"Quantitative Trait Loci". Quantitative Trait Loci (QTL) refers to genetic loci that control to some degree, numerically representable traits that are usually continuously distributed.

"Regeneration". Regeneration refers to the development of a plant from tissue culture.

"Resistance". As used herein the terms "resistance" and "tolerance" (and grammatical variations thereof) are used interchangeably to describe plants that show reduced or essentially no symptoms to a specific biotic (e.g., a pest, pathogen or disease) or abiotic (e.g., exogenous or environmental, including herbicides) factor or stressor. In some embodiments, "resistant" or "tolerant" plants show some symptoms but are still able to produce marketable product with an acceptable yield, e.g., the yield may still be reduced and/or the plants may be stunted as compared with the yield or growth in the absence of the biotic and/or abiotic factor or stressor. Those skilled in the art will appreciate that the degree of resistance or tolerance may be assessed with respect to a plurality or even an entire field of plants. A watermelon plant may be considered "resistant" or "tolerant" if resistance/tolerance is observed over a plurality of plants (e.g., an average), even if particular individual plants may be susceptible to the biotic or abiotic factor or stressor.

"RHS". RHS refers to the Royal Horticultural Society of England which publishes an official botanical color chart quantitatively identifying colors according to a defined numbering system. The chart may be purchased from Royal Horticulture Society Enterprise Ltd., RHS Garden; Wisley, Woking; Surrey GU236QB, UK.

"Single gene converted". A single gene converted or conversion plant refers to a plant that is developed by plant breeding techniques (e.g., backcrossing) or via genetic engineering wherein essentially all of the desired morphological and physiological characteristics of a line are recovered in addition to the single gene transferred into the line via the plant breeding technique or via genetic engineering.

"Substantially equivalent characteristic". A characteristic that, when compared, does not show a statistically significant difference (e.g., p=0.05) from the mean.

"Transgene". A nucleic acid of interest that can be introduced into the genome of a plant by genetic engineering techniques (e.g., transformation) or breeding. The transgene can be from the same or a different species. If from the same species, the transgene can be an additional copy of a native coding sequence or can present the native sequence in a form or context (e.g., different genomic location and/or in operable association with exogenous regulatory elements such as a promoter) than is found in the native state. The transgene can comprise an open reading frame encoding a polypeptide or can encode a functional non-translated RNA (e.g., RNAi).

Botanical Description of the Watermelon Line SP-7.

Characteristics. Diploid watermelon line SP-7 is characterized by a number of traits including, without limitation: small round fruits with a light green (Charleston Gray) skin color, brittle rind and yellow flesh; a dark brown mottled seed color, thin (lacy) vines, small leaves with deep lobes, and resistances to Anthracnose Race 1, *Fusarium* Wilt Races 1 and 2, and Powdery Mildew Race 1. SP-7 is further characterized by earlier presentation of male flowers and production of larger male flowers, with more male flowers at peak flowering time, as compared with SP-6.

Watermelon line SP-7 has shown uniformity and stability within the limits of environmental influence. It has been self-pollinated for numerous generations with careful attention to uniformity of plant type. The variety has been increased with continued observation for uniformity. No variant traits have been observed or are expected in watermelon line SP-7.

Watermelon cultivar SP-7 was compared with diploid watermelon cultivar SP-6 (U.S. Pat. No. 8,212,118 B1). Watermelon cultivar SP-6 was selected as the comparison variety because of its ploidy and similar maturity, fruit shape, skin appearance and plant type as compared with SP-7.

Figure 2:
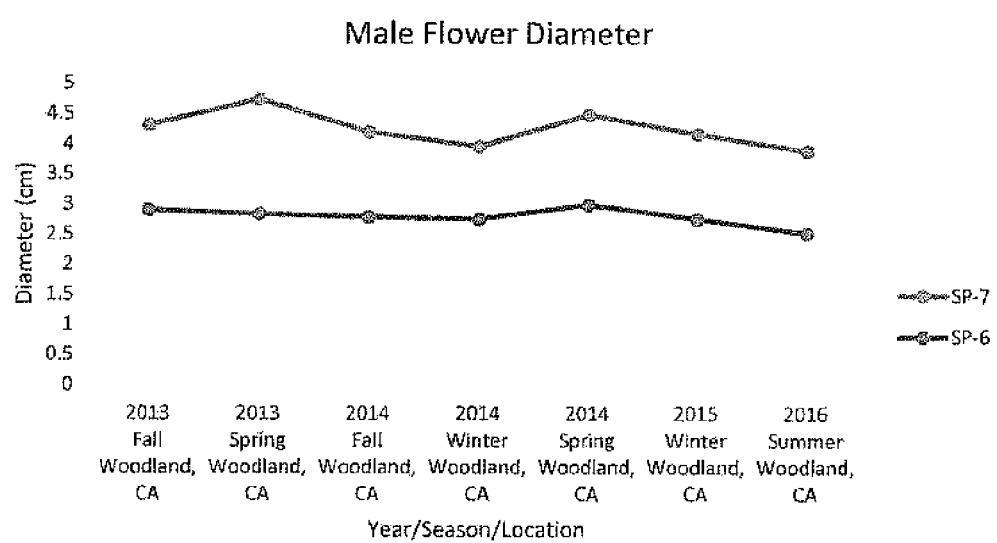
FIG. 2 shows male flower diameter (cm) of watermelon cultivars SP-7 (upper line) and SP-6 (lower line) as measured over multiple years. From 2013-2015, flower diameters were recorded in a greenhouse at the Woodland, Calif. station. In 2016, flower diameters were measured under open field cultivation in a replicated, randomized complete block design.
Figure 3:
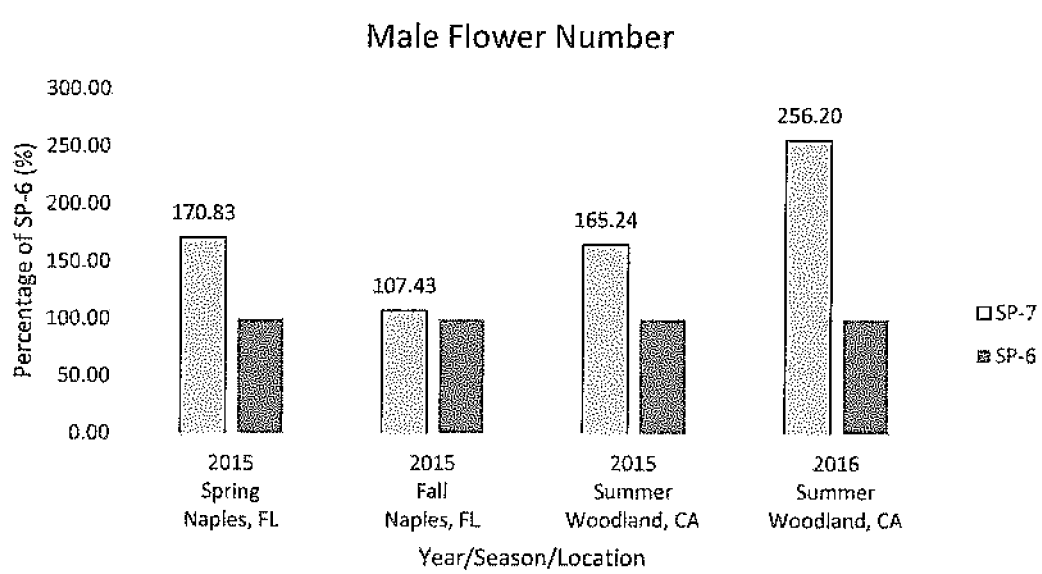
FIG. 3 shows the number of male flowers produced by watermelon cultivar SP-7 as a percentage of SP-6 male flower number, measured at peak flowering time. Male flower number was estimated by counting the number of open male flowers within a square meter of area. For each plot, two measurements were taken on a weekly basis. Peak flowering time was determined as the week when the most open male flowers were recorded across all plots. Data for SP-7 (left bars) are presented as a percentage of SP-6 (right bars; set at 100%), where % male flower=([SP-7 male flower number]÷[SP-6 male flower number])×100. The average percentages for SP-7 are indicated above the bars on the left.

Watermelon cultivar SP-7 can be distinguished from SP-6 at least on the basis of seed color, time to produce open male flowers, and the size and number of male flowers produced. The seed of SP-7 is a dark brown mottled color (RHS 200D) as compared with SP-6, which has a tan colored seed (RHS 164B). Watermelon cultivar SP-7 presents open male flowers at an earlier time point post-transplant as compared with SP-6 (FIG. 1, Example 1). In addition, SP-7 presents significantly larger male flowers than SP-6 (FIG. 2, Example 1), with significantly more male flowers being produced at the time of peak flowering (FIG. 3, Example 1).

A more detailed botanical description of SP-7 and comparison with SP-6 is shown in Table 1 below.

TABLE 1

Description of SP-7 and comparison with SP-6 based on open field trials in Woodland, California (summer, 2016).

| Characteristic: | SP-7 | SP-6 |
|---|---|---|
| General fruit type: | Round, very small | Round, very small |
| Area of best adaptation: | Most U.S. areas | Most U.S. areas |
| Maturity - No. of days from emergence of anthesis: | 19 | 23 |
| Maturity - No. of days from pollination to maturity: | 28 | 32 |
| Relative maturity (days): | 71 | 75 |
| Maturity category: | Medium | Medium |
| Ploidy: | Diploid | Diploid |
| Cotyledon shape: | Flat | Flat |
| Plant sex form: | Monoecious | Monoecious |
| Number of Main Stems at crown: | 4 | 7 |
| Number of flowers per plant at first fruit set: | 57.2 staminate 8 pistillate 2 perfect | 18.7 staminate 8 pistillate 2 perfect |
| Stem: | Round in cross-section, 7 mm diameter at second node, pubescent surface | Round in cross-section, 7 mm diameter at second node, pubescent surface |
| Vine length at last harvest (cm): | 330 | 330 |
| No. internodes at last harvest: | 38 | 38 |
| Ratio - cm vine length/internodes at last harvest: | 9 | 9 |
| Leaf shape: | Ovate | Ovate |
| Leaf lobes: | Lobed | Lobed |
| Leaf length (cm): | 13.3 | 16 |
| Leaf width (cm): | 8.5 | 8.3 |
| Leaf dorsal surface pubescence: | Smooth | Smooth |
| Leaf ventral surface pubescence: | Pubescent | Pubescent |
| Leaf color: | Dark green (RHS 137A) | Dark green (RHS 137A) |
| Flower: diameter across staminate (cm): | 3.9 | 2.2 |
| Flower: diameter across pistillate (cm): | 3.5 | 2.4 |
| Flower: diameter across perfect (cm): | Not applicable | Not applicable |
| Flower color: | Yellow (RHS 7D) | Yellow (RHS 7D) |
| Mature fruit shape: | Round | Round |
| Mature fruit length (cm): | 14.8 | 15 |
| Mature fruit diameter at midsection (cm); | 14.5 | 14 |
| Mature fruit average weight (kg) | 1.7 | 1.4 |
| Mature fruit maximum fruit weight (kg) | 3 | 2 |
| Mature fruit index = (length/diameter) × 10 | 10.2 | 11 |
| Mature fruit surface: | Smooth | Smooth |
| Mature fruit skin color pattern: | Solid | Mottle/Net |
| Mature fruit skin primary color: | Light green (Charleston Grey; RHS 143C) | Light green (Charleston Grey; RHS 143C) |
| Mature fruit skin secondary color: | Yellow green (RHS 160B) | Yellow green (RHS 160B) |
| Rind texture: | Brittle | Brittle |

TABLE 1-continued

Description of SP-7 and comparison with SP-6 based on open field trials in Woodland, California (summer, 2016).

| Characteristic: | SP-7 | SP-6 |
|---|---|---|
| Rind thickness blossom end (mm) | 5 | 5 |
| Rind thickness sides (mm) | 5 | 5 |
| Flesh texture: | Crisp | Crisp |
| Flesh coarseness: | Fine | Fine |
| Flesh color: | Yellow (RHS 7D) | Yellow (RHS 7D) |
| Flesh - Refractometer: % solids of juice (center of fruit): | 9.2 | 7 |
| Flesh % hollow heart: | 0 | 0 |
| Flesh % placental separation: | 0 | 0 |
| Flesh % transverse crack: | 0 | 0 |
| Seed (no seed in F1 fruit): | Large seed, 11 mm long × 6.3 mm wide × 2.6 mm thick; 77.4 gm per 1000 seeds; 240 seeds per fruit; dark brown mottled color (RHS 200D) | Large seed, 11 mm long × 6.5 mm wide × 2.3 mm thick; 72 gm per 1000 seeds; 590 seeds per fruit; tan color (RHS 163A) |
| Anthracnose, Race 1: | Resistant | Resistant |
| Fusarium Wilt, Race 1 and 2: | Resistant | Resistant |
| Powdery Mildew, Race 1: | Resistant | Resistant |

Tissue Culture.

In embodiments, watermelon plants can be propagated by tissue culture and regeneration. Tissue culture of various plant tissues and regeneration of plants therefrom is well known. For example, reference may be had to Teng, et al., HortScience, 27:9, 1030-1032 (1992); Teng, et al., HortScience, 28:6, 669-1671 (1993); Zhang, et al., Journal of Genetics and Breeding, 46:3, 287-290 (1992); Webb, et al., Plant Cell Tissue and Organ Culture, 38:1, 77-79 (1994); Curtis, et al., Journal of Experimental Botany, 45:279, 1441-1449 (1994); Nagata, et al., Journal for the American Society for Horticultural Science, 125:6, 669-672 (2000); and Ibrahim, et al., Plant Cell Tissue and Organ Culture, 28(2), 139-145 (1992). It is clear from the literature that the state of the art is such that these methods of obtaining plants are routinely used and have a high rate of success. Thus, another aspect of this invention is to provide cells which upon growth and differentiation produce watermelon plants having desired characteristics of watermelon line SP-7 (e.g., one or more of, small fruit, round fruit, a fruit with a light green (Charleston Gray) skin color, a fruit with a brittle rind, a fruit with yellow flesh; a dark brown mottled seed color, thin (lacy) vines, small leaves with deep lobes, one or more of the disease resistances of SP-7 (e.g., resistance to Anthracnose Race 1, resistance to *Fusarium* Wilt Races 1 and 2 and/or resistance to Powdery Mildew Race 1), earlier presentation of male flowers as compared with cultivar SP-6, production of larger male flowers as compared with cultivar SP-6 and/or production of more male flowers at peak flowering time as compared with SP-6, in any combination, e.g., as described in Table 1 and shown in FIGS. 1-3). Optionally, watermelon plants can be regenerated from the tissue culture of the invention comprising all or essentially all of the physiological and morphological characteristics of watermelon line SP-7.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, suckers, and the like. Means for preparing and maintaining plant tissue culture are well known in the art. By way of example, a tissue culture comprising organs has been used to produce regenerated plants. U.S. Pat. Nos. 5,959,185, 5,973,234, and 5,977,445 describe certain techniques.

Watermelon Pollenizers and Production of Seedless Watermelon Fruit

The primary use of dedicated watermelon pollenizers is to pollenize triploid watermelon plants to produce seedless watermelon fruit. Triploid watermelons are created by crossing a tetraploid (4X) female line with a diploid (2X) male line. The resulting triploid (3X) watermelon seeds are planted along with a diploid watermelon pollenizer line. The fruit produced on the triploid watermelon plants are seedless. Watermelon cultivar SP-7, a dedicated pollenizer that does not produce a harvestable fruit for consumption, can be planted in a narrower row than the triploid watermelon plants, thereby providing more field area for production of triploid seedless watermelon fruit as compared with a conventional pollenizer such as, for example, Sangria™ (Syngenta Seeds, Inc.).

An important use of watermelon cultivar SP-7 is to produce triploid, seedless watermelon fruit. The SP-7 pollenizer is used as the male parent to cross with a triploid female watermelon line to produce the triploid, seedless fruits.

Accordingly, the invention contemplates as one aspect a method of producing triploid seedless watermelon fruit, the method comprising: (a) crossing the watermelon plant of line SP-7 as a male parent with a triploid watermelon plant as the female parent; and (b) allowing triploid seedless watermelon fruit to form; and (c) optionally, harvesting the seedless fruit. In embodiments, the method comprises planting triploid watermelon seed/transplants and pollenizer SP-7 seed/transplants in one or more rows, and the plants are allowed to mature and develop seedless fruit. In embodiments, diploid and triploid seed/transplants are planted in the same row.

Additional Breeding Methods.

This invention is also directed to methods for producing a watermelon plant by crossing a first parent watermelon plant with a second parent watermelon plant wherein the first and/or second parent watermelon plant is a plant of watermelon line SP-7. In embodiments, both the first and second parent watermelon plants are diploid watermelon plants. Thus, any of the following exemplary methods using watermelon line SP-7 are part of this invention: selfing, backcrosses, hybrid production, crosses to populations, double haploid production, and the like. All plants produced using watermelon line SP-7 as at least one parent are within the scope of this invention, including those developed from watermelon plants derived from watermelon line SP-7. Advantageously, watermelon line SP-7 can be used in crosses with other, different, watermelon plants to produce first generation ($F_1$) watermelon hybrid seeds and plants with desirable characteristics. The watermelon plants of the invention can also be used for transformation where exogenous transgenes are introduced and expressed by the plants of the invention. Genetic variants created either through traditional breeding methods or through transformation of the cultivars of the invention by any of a number of protocols known to those of skill in the art are intended to be within the scope of this invention.

The following describes exemplary breeding methods that may be used with watermelon line SP-7 in the development of further watermelon plants. One such embodiment is a method for developing watermelon line SP-7 progeny watermelon plants (e.g., a diploid progeny watermelon plant) in a watermelon plant breeding program comprising: obtaining a plant, or a part thereof, of watermelon line SP-7, utilizing said plant or plant part as a source of breeding material, and selecting a watermelon line SP-7 progeny plant with molecular markers in common with watermelon line SP-7 and/or with some, all or essentially all morphological and/or physiological characteristics of watermelon line SP-7 (see, e.g., Table 1 and FIGS. 1-3). In representative embodiments, the progeny plant has at least 1, 2, 3, 4, 5, 6, 7, 8, 9, 10 or more of the morphological and physiological characteristics of watermelon line SP-7 (for example, one or more of small fruit, round fruit, a fruit with a light green [Charleston Gray] skin color, a fruit with a brittle rind, a fruit with yellow flesh; a dark brown mottled seed color, thin (lacy) vines, small leaves with deep lobes, one or more of the disease resistances of SP-7 [e.g., resistance to Anthracnose Race 1, resistance to *Fusarium* Wilt Races 1 and 2 and/or resistance to Powdery Mildew Race 1], earlier presentation of male flowers as compared with cultivar SP-6, production of larger male flowers as compared with cultivar SP-6 and/or production of more male flowers at peak flowering time as compared with SP-6, in any combination, e.g., as described in Table 1 and shown in FIGS. 1-3), or even all of the morphological and physiological characteristics of watermelon line SP-7 so that said progeny watermelon plant is not significantly different for said traits than watermelon line SP-7, as determined at the 5% significance level when grown in the same environmental conditions; optionally, with the presence of one or more desired additional traits (e.g., male sterility, disease resistance, pest or insect resistance, herbicide resistance, and the like). Breeding steps that may be used in the breeding program include pedigree breeding, backcrossing, mutation breeding and/or recurrent selection. In conjunction with these steps, techniques such as RFLP-enhanced selection, genetic marker enhanced selection (for example, SSR markers) and/or and the making of double haploids may be utilized.

Another representative method involves producing a population of watermelon line SP-7 progeny plants (e.g., diploid progeny plants), comprising crossing watermelon line SP-7 with another watermelon plant (e.g., a diploid watermelon plant), thereby producing a population of watermelon plants that, on average, derives at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line SP-7, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line SP-7. One embodiment of this invention is the watermelon plant produced by this method and that has obtained at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line SP-7, and optionally may be the result of a breeding process comprising one or two breeding crosses and one or more of selfing, sibbing, backcrossing and/or double haploid techniques in any combination and any order. In embodiments, the breeding process does not include a breeding cross, and comprises selfing, sibbing, backcrossing and or double haploid technology.

One of ordinary skill in the art of plant breeding would know how to evaluate the traits of two plant varieties to determine if there is or is not significant difference between the two traits expressed by those varieties. For example, see Fehr and Walt, Principles of Cultivar Development, pp. 261-286 (1987). Thus, the invention includes watermelon line SP-7 progeny watermelon plants characterized by e.g., one or more of small fruit, round fruit, a fruit with a light green (Charleston Gray) skin color, a fruit with a brittle rind, a fruit with yellow flesh; a dark brown mottled seed color, thin (lacy) vines, small leaves with deep lobes, one or more of the disease resistances of SP-7 (e.g., resistance to Anthracnose Race 1, resistance to *Fusarium* Wilt Races 1 and 2 and/or resistance to Powdery Mildew Race 1), earlier presentation of male flowers as compared with cultivar SP-6, production of larger male flowers as compared with cultivar SP-6 and/or production of more male flowers at peak flowering time as compared with SP-6, in any combination. In embodiments, the invention encompasses progeny plants having a combination of at least 2, 3, 4, 5, 6, 7, 8, 9, 10 or more of the characteristics as described herein for watermelon line SP-7, so that said progeny watermelon plant is not significantly different for said traits than watermelon line SP-7, as determined at the 5% significance level when grown in the same environmental conditions. Using techniques described herein and those known in the art, molecular markers may be used to identify said progeny plant as progeny of watermelon line SP-7. Mean trait values may be used to determine whether trait differences are significant, and optionally the traits are measured on plants grown under the same environmental conditions.

Progeny of watermelon line SP-7 may also be characterized through their filial relationship with watermelon line SP-7, as for example, being within a certain number of breeding crosses of watermelon line SP-7. A breeding cross is a cross made to introduce new genetics into the progeny, and is distinguished from a cross, such as a self or a sib cross or a backcross to SP-7 as a recurrent parent, made to select among existing genetic alleles. The lower the number of breeding crosses in the pedigree, the closer the relationship between watermelon line SP-7 and its progeny. For example, progeny produced by the methods described herein may be within 1, 2, 3, 4, 5 or more breeding crosses of watermelon line SP-7.

In representative embodiments, a watermelon plant derived from watermelon line SP-7 comprises cells comprising at least one set of chromosomes derived from watermelon line SP-7. In embodiments, the watermelon plant or population of watermelon plants derived from watermelon line SP-7 comprises, on average, at least 6.25%, 12.5%, 25%, 30%, 35%, 40%, 45%, 50%, 55%, 60%, 65%, 70%, 80%, 85%, 90%, 95%, 96%, 97%, 98% or 99% of its alleles (i.e., TAC) from watermelon line SP-7, e.g., at least about 6.25%, 12.5%, 25%, 30%, 35%, 40%, 45%, 50%, 55%, 60%, 65%, 70%, 80%, 85%, 90%, 95%, 96%, 97%, 98% or 99% of the genetic complement of watermelon line SP-7, and optionally may be the result of one or more of selfing, sibbing, backcrossing and/or double haploid techniques in any combination. In embodiments, the watermelon plant derived from watermelon line SP-7 is one, two, three, four, five or more breeding crosses removed from watermelon line SP-7.

In representative embodiments, a plant derived from watermelon line SP-7 is a double haploid plant, a hybrid plant, an inbred plant, a tetraploid plant, a triploid plant and/or a diploid plant.

In embodiments, a derived plant from watermelon line SP-7 comprises a desired added trait. In representative embodiments, a watermelon plant derived from watermelon line SP-7 comprises all of the morphological and physiological characteristics of watermelon line SP-7 (e.g., as described in Table 1 and FIGS. 1-3). In embodiments, the watermelon plant derived from watermelon line SP-7 comprises essentially all of the morphological and physiological characteristics of watermelon line SP-7 (e.g., as described in Table 1 and FIGS. 1-3), with the addition of a desired added trait.

Those skilled in the art will appreciate that any of the traits described herein with respect to plant transformation methods can be introduced into a plant of the invention (e.g., watermelon line SP-7 and hybrid watermelon plants and other watermelon plants derived therefrom) using breeding techniques.

Further Embodiments of the Invention.

With the advent of molecular biological techniques that have allowed the isolation and characterization of genes that encode specific protein products, scientists in the field of plant biology developed a strong interest in engineering the genome of plants to contain and express foreign nucleic acids including additional or modified versions of native (endogenous) nucleic acids (optionally driven by a non-native promoter) in order to alter the traits of a plant in a specific manner. Any nucleic acid sequences, whether from a different species or from the same species, which are introduced into the genome using transformation or various breeding methods, are referred to herein collectively as "transgenes." Over the last fifteen to twenty years, several methods for producing transgenic plants have been developed, and in particular embodiments the present invention also relates to transformed versions of watermelon plants disclosed herein.

Genetic engineering techniques can be used (alone or in combination with breeding methods) to introduce one or more desired added traits into plant, for example, watermelon line SP-7 or progeny or watermelon plants derived thereof.

Plant transformation generally involves the construction of an expression vector that will function in plant cells. Optionally, such a vector comprises one or more nucleic acids comprising a coding sequence for a polypeptide or an untranslated functional RNA under control of, or operatively linked to, a regulatory element (for example, a promoter). In representative embodiments, the vector(s) may be in the form of a plasmid, and can be used alone or in combination with other plasmids, to provide transformed watermelon plants using transformation methods as described herein to incorporate transgenes into the genetic material of the watermelon plant.

Additional methods include, but are not limited to, expression vectors introduced into plant tissues using a direct nucleic acid transfer method, such as microprojectile-mediated delivery (e.g., with a biolistic device), DNA injection, *Agrobacterium*-mediated transformation, electroporation, and the like. Transformed plants obtained from the plants (and parts and tissue culture thereof) of the invention are intended to be within the scope of this invention.

Expression Vectors for Plant Transformation—Selectable Markers.

Expression vectors typically include at least one nucleic acid comprising or encoding a selectable marker, operably linked to a regulatory element (for example, a promoter) that allows transformed cells containing the marker to be either recovered by negative selection, e.g., inhibiting growth of cells that do not contain the selectable marker, or by positive selection, e.g., screening for the product encoded by the selectable marker. Many commonly used selectable markers for plant transformation are well known in the transformation art, and include, for example, nucleic acids that code for enzymes that metabolically detoxify a selective chemical agent which may be an antibiotic or an herbicide, or nucleic acids that encode an altered target which is insensitive to the inhibitor. Positive selection methods are also known in the art.

One commonly used selectable marker for plant transformation is a neomycin phosphotransferase II (nptII) coding sequence, for example, isolated from transposon Tn5, which when placed under the control of plant regulatory signals confers resistance to kanamycin. Fraley, et al., PNAS, 80:4803 (1983). Another commonly used selectable marker is hygromycin phosphotransferase, which confers resistance to the antibiotic hygromycin. Vanden Elzen, et al., Plant Mol. Biol., 5:299 (1985).

Additional selectable markers of bacterial origin that confer resistance to antibiotics include gentamycin acetyl transferase, streptomycin phosphotransferase, aminoglycoside-3'-adenyl transferase, the bleomycin resistance determinant. Hayford, et al., Plant Physiol., 86:1216 (1988); Jones, et al., Mol. Gen. Genet., 210:86 (1987); Svab, et al., Plant Mol. Biol., 14:197 (1990); Hille, et al., Plant Mol. Biol., 7:171 (1986). Other selectable markers confer resistance to herbicides such as glyphosate, glufosinate, or bromoxynil. Comai, et al., Nature, 317:741-744 (1985); Gordon-Kamm, et al., Plant Cell, 2:603-618 (1990); and Stalker, et al., Science, 242:419-423 (1988).

Selectable markers for plant transformation that are not of bacterial origin include, for example, mouse dihydrofolate reductase, plant 5-enolpyruvylshikimate-3-phosphate synthase, and plant acetolactate synthase. Eichholtz, et al., Somatic Cell Mol. Genet., 13:67 (1987); Shah, et al., Science, 233:478 (1986); and Charest, et al., Plant Cell Rep., 8:643 (1990).

Another class of selectable marker for plant transformation involves screening of presumptively transformed plant cells rather than direct genetic selection of transformed cells for resistance to a toxic substance such as an antibiotic. These selectable markers are particularly useful to quantify or visualize the spatial pattern of expression of a transgene in specific tissues and are frequently referred to as a reporter gene because they can be fused to transgene or regulatory sequence for the investigation of nucleic acid expression. Commonly used reporters for screening presumptively transformed cells include alpha-glucuronidase (GUS), alpha-galactosidase, luciferase and chloramphenicol, acetyltransferase. Jefferson, R. A., Plant Mol. Biol., 5:387 (1987); Teeri, et al., EMBO J., 8:343 (1989); Koncz, et al., PNAS, 84:131 (1987); and DeBlock, et al., EMBO J., 3:1681 (1984).

In vivo methods for visualizing GUS activity that do not require destruction of plant tissues are available. Molecular Probes, Publication 2908, IMAGENE GREEN, pp. 1-4 (1993) and Naleway, et al., J. Cell Biol., 115:151a (1991).

Green Fluorescent Protein (GFP) is also utilized as a marker for nucleic acid expression in prokaryotic and eukaryotic cells. Chalfie, et al., Science, 263:802 (1994). GFP and mutants of GFP may be used as screenable markers.

Expression Vectors for Plant Transformation—Promoters.

Transgenes included in expression vectors are generally driven by a nucleotide sequence comprising a regulatory element (for example, a promoter). Numerous types of promoters are well known in the transformation arts, as are other regulatory elements that can be used alone or in combination with promoters.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells.

Examples of promoters under developmental control include promoters that preferentially initiate transcription in certain tissues, such as leaves, roots, seeds, fibers, xylem vessels, tracheids, or sclerenchyma. Such promoters are referred to as "tissue-preferred." Promoters that initiate transcription only in certain tissue are referred to as "tissue-specific." A "cell type" specific promoter preferentially drives expression in certain cell types in one or more organs, for example, vascular cells in roots or leaves. An "inducible" promoter is a promoter that is under environmental control. Examples of environmental conditions that may affect transcription by inducible promoters include anaerobic conditions or the presence of light. Tissue-specific, tissue-preferred, cell type specific, and inducible promoters constitute the class of "non-constitutive" promoters. A "constitutive" promoter is a promoter that is active under most environmental conditions.

A. Inducible Promoters:

An inducible promoter is operably linked to a nucleic acid for expression in a plant. Optionally, the inducible promoter is operably linked to a nucleotide sequence encoding a signal sequence which is operably linked to a nucleic acid for expression in the plant. With an inducible promoter, the rate of transcription increases in response to an inducing agent.

Any inducible promoter can be used in the instant invention. See Ward, et al., Plant Mol. Biol., 22:361-366 (1993). Exemplary inducible promoters include, but are not limited to, that from the ACEI system which responds to copper (Melt, et al., PNAS, 90:4567-4571 (1993)); promoter from the In2 gene from maize which responds to benzenesulfonamide herbicide safeners (Hershey, et al., Mol. Gen. Genet., 227:229-237 (1991) and Gatz, et al., Mol. Gen. Genet., 243:32-38 (1994)) or Tet repressor from Tn10 (Gatz, et al., Mol. Gen. Genet., 227:229-237 (1991)). A representative inducible promoter is a promoter that responds to an inducing agent to which plants do not normally respond. An exemplary inducible promoter is the inducible promoter from a steroid hormone gene, the transcriptional activity of which is induced by a glucocorticosteroid hormone. Schena, et al., PNAS, 88:0421 (1991).

B. Constitutive Promoters:

A constitutive promoter is operably linked to a nucleic acid for expression in a plant or the constitutive promoter is operably linked to a nucleotide sequence encoding a signal sequence which is operably linked to a nucleic acid for expression in a plant.

Many different constitutive promoters can be utilized in the instant invention. Exemplary constitutive promoters include, but are not limited to, the promoters from plant viruses such as the 35S promoter from CaMV (Odell, et al., Nature, 313:810-812 (1985)) and the promoters from such genes as rice actin (McElroy, et al., Plant Cell, 2:163-171 (1990)); ubiquitin (Christensen, et al., Plant Mol. Biol., 12:619-632 (1989) and Christensen, et al., Plant Mol. Biol., 18:675-689 (1992)); pEMU (Last, et al., Theor. Appl. Genet., 81:581-588 (1991)); MAS (Velten, et al., EMBO J., 3:2723-2730 (1984)) and maize H3 histone (Lepetit, et al., Mol. Gen. Genet., 231:276-285 (1992) and Atanassova, et al., Plant J., 2 (3):291-300 (1992)). The ALS promoter, Xbal/Ncol fragment 5' to the *Brassica napus* ALS3 structural gene (or a nucleotide sequence similarity to said Xbal/Ncol fragment), represents a particularly useful constitutive promoter. See PCT Application No. WO 96/30530.

C. Tissue-Specific or Tissue-Preferred Promoters:

A tissue-specific promoter is operably linked to a nucleic acid for expression in a plant. Optionally, the tissue-specific promoter is operably linked to a nucleotide sequence encoding a signal sequence which is operably linked to a nucleic acid for expression in a plant. Plants transformed with a nucleic acid of interest operably linked to a tissue-specific promoter transcribe the nucleic acid of interest exclusively, or preferentially, in a specific tissue.

Any tissue-specific or tissue-preferred promoter can be utilized in the instant invention. Exemplary tissue-specific or tissue-preferred promoters include, but are not limited to, a root-preferred promoter, such as that from the phaseolin gene (Murai, et al., Science, 23:476-482 (1983) and Sengupta-Gopalan, et al., PNAS, 82:3320-3324 (1985)); a leaf-specific and light-induced promoter such as that from cab or rubisco (Simpson, et al., EMBO J., 4(11):2723-2729 (1985) and Timko, et al., Nature, 318:579-582 (1985)); an anther-specific promoter such as that from LAT52 (Twell, et al., Mol. Gen. Genet., 217:240-245 (1989)); a pollen-specific promoter such as that from Zm13 (Guerrero, et al., Mol. Gen. Genet., 244:161-168 (1993)) or a microspore-preferred promoter such as that from apg (Twell, et al., Sex. Plant Reprod., 6:217-224 (1993)).

Signal Sequences for Targeting Proteins to Subcellular Compartments.

Transport of polypeptides produced by transgenes to a subcellular compartment such as the chloroplast, vacuole, peroxisome, glyoxysome, cell wall, or mitochondrion, or for secretion into the apoplast, is generally accomplished by means of operably linking a nucleotide sequence encoding a signal sequence to the 5' and/or 3' region of a nucleic acid encoding the polypeptide of interest. Signal sequences at the 5' and/or 3' end of the coding sequence target the polypeptide to particular subcellular compartments.

The presence of a signal sequence can direct a polypeptide to either an intracellular organelle or subcellular compartment or for secretion to the apoplast. Many signal sequences are known in the art. See, for example, Becker, et al., Plant Mol. Biol., 20:49 (1992); Close, P. S., Master's Thesis, Iowa State University (1993); Knox, C., et al., "Structure and Organization of Two Divergent Alpha-Amylase Genes from Barley," Plant Mol. Biol., 9:3-17 (1987); Lerner, et al., Plant Physiol., 91:124-129 (1989); Fontes, et al., Plant Cell, 3:483-496 (1991); Matsuoka, et al., PNAS, 88:834 (1991); Gould, et al., J. Cell. Biol., 108:1657 (1989); Creissen, et al., Plant J, 2:129 (1991); Kalderon, et al., A short amino acid sequence able to specify nuclear location, Cell, 39:499-509 (1984); and Steifel, et al., Expression of a maize cell wall hydroxyproline-rich glycoprotein gene in early leaf and root vascular differentiation, Plant Cell, 2:785-793 (1990).

Foreign Polypeptide Transgenes and Agronomic Transgenes.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign polypeptide then can be extracted from a tissue of interest or from total biomass. Protein extraction from plant biomass can be accomplished by known methods which are discussed, for example, by Heney and Orr, Anal. Biochem., 114:92-6 (1981).

According to a representative embodiment, the transgenic plant provided for commercial production of foreign protein is a watermelon plant of the invention. In another embodiment, the biomass of interest is seed. For the relatively small number of transgenic plants that show higher levels of expression, a genetic map can be generated, for example via conventional RFLP, PCR, and SSR analysis, which identifies the approximate chromosomal location of the integrated DNA molecule. For exemplary methodologies in this regard, see Methods in Plant Molecular Biology and Biotechnology, Glick and Thompson Eds., 269:284, CRC Press, Boca Raton (1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons can involve hybridizations, RFLP, PCR, SSR, and sequencing, all of which are conventional techniques.

Likewise, by means of the present invention, agronomic transgenes and other desired added traits can be expressed in transformed plants (and their progeny, e.g., produced by breeding methods). More particularly, plants can be genetically engineered to express various phenotypes of agronomic interest or other desired added traits. Exemplary nucleic acids of interest in this regard conferring a desired added trait(s) include, but are not limited to, those categorized below:

A. Transgenes that Confer Resistance to Pests or Disease:

1. Plant disease resistance transgenes. Plant defenses are often activated by specific interaction between the product of a disease resistance gene (R) in the plant and the product of a corresponding avirulence (Avr) gene in the pathogen. A plant line can be transformed with a cloned resistance transgene to engineer plants that are resistant to specific pathogen strains. See, for example, Jones, et al., Science, 266:789 (1994) (cloning of the tomato Cf-9 gene for resistance to *Cladosporium fulvum*); Martin, et al., Science, 262:1432 (1993) (tomato Pto gene for resistance to *Pseudomonas syringae* pv. tomato encodes a protein kinase); and Mindrinos, et al., Cell, 78:1089 (1994) (*Arabidopsis* RSP2 gene for resistance to *Pseudomonas syringae*).

2. A *Bacillus thuringiensis* protein, a derivative thereof, or a synthetic polypeptide modeled thereon. See, for example, Geiser, et al., Gene, 48:109 (1986), who disclose the cloning and nucleotide sequence of a Bt delta-endotoxin gene. Moreover, DNA molecules encoding delta-endotoxin transgenes can be purchased from American Type Culture Collection, Manassas, Va., for example, under ATCC Accession Nos. 40098, 67136, 31995, and 31998.

3. A lectin. See, for example, the disclosure by Van Damme, et al., Plant Mol. Biol., 24:25 (1994), who disclose the nucleotide sequences of several *Clivia miniata* mannose-binding lectin transgenes.

4. A vitamin-binding protein such as avidin. See, e.g., PCT Application No. US 93/06487. The application teaches the use of avidin and avidin homologues as larvicides against insect pests.

5. An enzyme inhibitor, for example, a protease or proteinase inhibitor, or an amylase inhibitor. See, for example, Abe, et al., J. Biol. Chem., 262:16793 (1987) (nucleotide sequence of rice cysteine proteinase inhibitor); Huub, et al., Plant Mol. Biol., 21:985 (1993) (nucleotide sequence of cDNA encoding tobacco proteinase inhibitor I); and Sumitani, et al., Biosci. Biotech. Biochem., 57:1243 (1993) (nucleotide sequence of *Streptomyces nitrosporeus* alpha-amylase inhibitor).

6. An insect-specific hormone or pheromone, such as an ecdysteroid and juvenile hormone, a variant thereof, a mimetic based thereon, or an antagonist or agonist thereof. See, for example, the disclosure by Hammock, et al., Nature, 344:458 (1990), of baculovirus expression of cloned juvenile hormone esterase, an inactivator of juvenile hormone.

7. An insect-specific peptide or neuropeptide which, upon expression, disrupts the physiology of the affected pest. For example, see the disclosures of Regan, J. Biol. Chem., 269:9 (1994) (expression cloning yields DNA coding for insect diuretic hormone receptor) and Pratt, et al., Biochem. Biophys. Res. Comm., 163:1243 (1989) (an allostatin is identified in *Diploptera puntata*). See also, U.S. Pat. No. 5,266,317 to Tomalski, et al., who disclose transgenes encoding insect-specific, paralytic neurotoxins.

8. An insect-specific venom produced in nature, by a snake, a wasp, etc. For example, see Pang, et al, Gene, 116:165 (1992), for disclosure of heterologous expression in plants of a transgene coding for a scorpion insectotoxic peptide.

9. An enzyme responsible for a hyper-accumulation of a monoterpene, a sesquiterpene, a steroid, hydroxamic acid, a phenylpropanoid derivative, or another non-protein molecule with insecticidal activity.

10. An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase, and a glucanase, whether natural or synthetic. See PCT Application No. WO 93/02197 in the name of Scott, et al., which discloses the nucleotide sequence of a callase transgene. DNA molecules which contain chitinase-encoding sequences can be obtained, for example, from the ATCC under Accession Nos. 39637 and 67152. See also, Kramer, et al., Insect Biochem. Mol. Biol., 23:691 (1993), who teach the nucleotide sequence of a cDNA encoding tobacco hornworm chitinase, and Kawalleck, et al., Plant Mol. Biol., 21:673 (1993), who provide the nucleotide sequence of the parsley ubi4-2 polyubiquitin transgene.

11. A molecule that stimulates signal transduction. For example, see the disclosure by Botella, et al., Plant Mol. Biol., 24:757 (1994), of nucleotide sequences for mung bean calmodulin cDNA clones, and Griess, et al., Plant Physiol., 104:1467 (1994), who provide the nucleotide sequence of a maize calmodulin cDNA clone.

12. A hydrophobic moment peptide. See PCT Application No. WO 95/16776 (disclosure of peptide derivatives of tachyplesin which inhibit fungal plant pathogens) and PCT Application No. WO 95/18855 (teaches synthetic antimicrobial peptides that confer disease resistance).

13. A membrane permease, a channel former, or a channel blocker. For example, see the disclosure of Jaynes, et al., Plant Sci., 89:43 (1993), of heterologous expression of a cecropin-beta, lytic peptide analog to render transgenic tobacco plants resistant to *Pseudomonas solanacearum*.

14. A viral-invasive protein or a complex toxin derived therefrom. For example, the accumulation of viral coat proteins in transformed plant cells imparts resistance to viral infection and/or disease development effected by the virus from which the coat protein transgene is derived, as well as by related viruses. See Beachy, et al., Ann. Rev. Phytopathol., 28:451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus, and tobacco mosaic virus. Id.

15. An insect-specific antibody or an immunotoxin derived therefrom. Thus, an antibody targeted to a critical metabolic function in the insect gut would inactivate an affected enzyme, killing the insect. See Taylor, et al., Abstract #497, Seventh Intl Symposium on Molecular Plant-Microbe Interactions, Edinburgh, Scotland (1994) (enzymatic inactivation in transgenic tobacco via production of single-chain antibody fragments).

16. A virus-specific antibody. See, for example, Tavladoraki, et al., Nature, 366:469 (1993), who show that transgenic plants expressing recombinant antibody transgenes are protected from virus attack.

17. A developmental-arrestive protein produced in nature by a pathogen or a parasite. Thus, fungal endo-alpha-1,4-D-polygalacturonases facilitate fungal colonization and plant nutrient released by solubilizing plant cell wall homo-alpha-1,4-D-galacturonase. See Lamb, et al., Bio/technology, 10:1436 (1992). The cloning and characterization of a transgene which encodes a bean endopolygalacturonase-inhibiting protein is described by Toubart, et al., Plant J., 2:367 (1992).

18. A developmental-arrestive protein produced in nature by a plant. For example, Logemann, et al., Bio/technology, 10:305 (1992), have shown that transgenic plants expressing the barley ribosome-inactivating transgene have an increased resistance to fungal disease.

19. A watermelon mosaic potyvirus (LMV) coat protein transgene introduced into *Lactuca sativa* in order to increase its resistance to LMV infection. See Dinant, et al., Mol. Breeding, 3:1, 75-86 (1997).

Any disease or present resistance transgenes, including those exemplified above, can be introduced into a watermelon plant of the invention through a variety of means including but not limited to transformation and breeding.

B. Transgenes that Confer Resistance to an Herbicide:

Exemplary polynucleotides encoding polypeptides that confer traits desirable for herbicide resistance include acetolactate synthase (ALS) mutants that lead to herbicide resistance such as the S4 and/or Hra mutations ((resistance to herbicides including sulfonylureas, imidazolinones, triazolopyrimidines, pyrimidinyl thiobenzoates); glyphosate resistance (e.g., 5-enol-pyrovyl-shikimate-3-phosphate-synthase (EPSPS) transgene, including but not limited to those described in U.S. Pat. Nos. 4,940,935, 5,188,642, 5,633,435, 6,566,587, 7,674,598 as well as all related application; or the glyphosate N-acetyltransferase (GAT) transgene, described in Castle et al., Science, 2004, 304:1151-1154; and in U.S. Patent Application Publication Nos. 20070004912, 20050246798, and 20050060767)); glufosinate resistance (e.g., BAR; see e.g., U.S. Pat. No. 5,561,236); 2,4-D resistance (e.g., aryloxy alkanoate dioxygenase or AAD-1, AAD-12, or AAD-13), HPPD resistance (e.g., *Pseudomonas* HPPD) and PPO resistance (e.g., fomesafen, acifluorfen-sodium, oxyfluorfen, lactofen, fluthiacet-methyl, saflufenacil, flumioxazin, flumiclorac-pentyl, carfentrazone-ethyl, sulfentrazone); a cytochrome P450 or variant thereof that confers herbicide resistance or tolerance to, inter alia, HPPD-inhibiting herbicides, PPO-inhibiting herbicides and ALS-inhibiting herbicides (U.S. Patent Application Publication No. 20090011936; U.S. Pat. Nos. 6,380,465; 6,121,512; 5,349,127; 6,649,814; and 6,300,544; and PCT International Publication No. WO 2007/000077); dicamba resistance (e.g., dicamba monoxygenase), and traits desirable for processing or process products such as high oil (e.g., U.S. Pat. No. 6,232,529); modified oils (e.g., fatty acid desaturase transgenes (U.S. Pat. No. 5,952,544; PCT International Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al., J. Bacteriol., 1988, 170:5837-5847) facilitate expression of polyhydroxyalkanoates (PHAs)).

In embodiments, the polynucleotide encodes a polypeptide conferring resistance to an herbicide selected from glyphosate, sulfonylurea, imidazolinone, dicamba, glufosinate, phenoxy proprionic acid, L-phosphinothricin, cyclohexone, cyclohexanedione, triazine, and benzonitrile.

Any transgene conferring herbicide resistance, including those exemplified above, can be introduced into the watermelon plants of the invention through a variety of means including, but not limited to, transformation (e.g., genetic engineering techniques) and crossing.

C. Transgenes that Confer or Contribute to a Value-Added Trait:

1. Increased iron content of the watermelon, for example, by introducing into a plant a soybean ferritin transgene as described in Goto, et al., *Acta Horticulturae.*, 521, 101-109 (2000).

2. Decreased nitrate content of leaves, for example, by introducing into a watermelon a transgene coding for a nitrate reductase. See, for example, Curtis, et al., *Plant Cell Rep.*, 18:11, 889-896 (1999).

3. Increased sweetness of the watermelon by introducing a transgene coding for monellin that elicits a flavor 100,000 times sweeter than sugar on a molar basis. See Penarrubia, et al., *Bio/technology*, 10:561-564 (1992).

4. Modified fatty acid metabolism, for example, by introducing into a plant an antisense sequence directed against stearyl-ACP desaturase to increase stearic acid content of the plant. See Knultzon, et al., PNAS, 89:2625 (1992).

5. Modified carbohydrate composition effected, for example, by introducing into plants a transgene coding for an enzyme that alters the branching pattern of starch. See Shiroza, et al., J. Bacteria, 170:810 (1988) (nucleotide sequence of *Streptococcus* mutants fructosyltransferase transgene); Steinmetz, et al., Mol. Gen. Genet., 20:220 (1985) (nucleotide sequence of *Bacillus subtilis* levansucrase transgene); Pen, et al., Bio/technology, 10:292 (1992) (production of transgenic plants that express *Bacillus lichenifonnis* alpha-amylase); Elliot, et al., Plant Mol. Biol., 21:515 (1993) (nucleotide sequences of tomato invertase transgenes); Sogaard, et al., J. Biol. Chem., 268:22480 (1993) (site-directed mutagenesis of barley alpha-amylase transgene); and Fisher, et al., Plant Physiol., 102:1045 (1993) (maize endosperm starch branching enzyme II).

Any transgene that confers or contributes a value-added trait, including those exemplified above, can be introduced into the watermelon plants of the invention through a variety of means including, but not limited to, transformation (e.g., genetic engineering techniques) and crossing.

D. Transgenes that Control Male-Sterility:

1. Introduction of a deacetylase transgene under the control of a tapetum-specific promoter and with the application of the chemical N—Ac-PPT. See, e.g., International Publication WO 01/29237.

2. Introduction of various stamen-specific promoters. See, e.g., International Publications WO 92/13956 and WO 92/13957.

3. Introduction of the barnase and the barstar transgenes. See, e.g., Paul, et al., Plant Mol. Biol., 19:611-622 (1992).

Any transgene that controls male sterility, including those exemplified above, can be introduced into the watermelon plants of the invention through a variety of means including, but not limited to, transformation (e.g., genetic engineering techniques) and crossing.

Methods for Plant Transformation.

Numerous methods for plant transformation have been developed, including biological and physical, plant transformation protocols. See, for example, Miki, et al., "Procedures for Introducing Foreign DNA into Plants" in Methods in Plant Molecular Biology and Biotechnology, Glick and Thompson Eds., CRC Press, Inc., Boca Raton, pp. 67-88 (1993). In addition, expression vectors and in vitro culture methods for plant cell or tissue transformation and regeneration of plants are available. See, for example, Gruber, et al., "Vectors for Plant Transformation" in Methods in Plant Molecular Biology and Biotechnology, Glick and Thompson Eds., CRC Press, Inc., Boca Raton, pp. 89-119 (1993).

A. *Agrobacterium*-Mediated Transformation.

One method for introducing an expression vector into plants is based on the natural transformation system of *Agrobacterium*. See, for example, Horsch, et al., Science, 227:1229 (1985); Curtis, et al., Journal of Experimental Botany, 45:279, 1441-1449 (1994); Torres, et al., Plant Cell Tissue and Organ Culture, 34:3, 279-285 (1993); and Dinant, et al., Molecular Breeding, 3:1, 75-86 (1997). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., Crit. Rev. Plant Sci., 10:1 (1991). Descriptions of *Agrobacterium* vector systems and methods for *Agrobacterium*-mediated transgene transfer are provided by Gruber, et al., supra, Miki, et al., supra, and Moloney, et al., Plant Cell Rep., 8:238 (1989). See also, U.S. Pat. No. 5,591,616 issued Jan. 7, 1997.

B. Direct Transgene Transfer.

Several methods of plant transformation collectively referred to as direct transgene transfer have been developed as an alternative to *Agrobacterium*-mediated transformation. A generally applicable method of plant transformation is microprojectile-mediated transformation wherein DNA is carried on the surface of microprojectiles measuring 1 micron to 4 micron. The expression vector is introduced into plant tissues with a biolistic device that accelerates the microprojectiles to speeds of 300 m/s to 600 m/s which is sufficient to penetrate plant cell walls and membranes. Russell, D. R., et al., Plant Cell Rep., 12 (3, January), 165-169 (1993); Aragao, F. J. L., et al., Plant Mol. Biol., 20 (2, October), 357-359 (1992); Aragao, F. J. L., et al., Plant Cell Rep., 12 (9, July), 483-490 (1993); Aragao, Theor. Appl. Genet., 93:142-150 (1996); Kim, J., Minamikawa, T., Plant Sci., 117:131-138 (1996); Sanford, et al., Part. Sci. Technol., 5:27 (1987); Sanford, J. C., Trends Biotech., 6:299 (1988); Klein, et al., Bio/technology, 6:559-563 (1988); Sanford, J. C., Physiol. Plant, 7:206 (1990); Klein, et al., Bio/technology, 10:268 (1992).

Another method for physical delivery of DNA to plants is sonication of target cells. Zhang, et al., Bio/technology, 9:996 (1991). Alternatively, liposome and spheroplast fusion have been used to introduce expression vectors into plants. Deshayes, et al., EMBO J., 4:2731 (1985) and Christou, et al., PNAS, 84:3962 (1987). Direct uptake of DNA into protoplasts using $CaCl_2$ precipitation, polyvinyl alcohol, or poly-L-ornithine has also been reported. Hain, et al., Mol. Gen. Genet., 199:161 (1985) and Draper, et al., Plant Cell Physiol., 23:451 (1982). Electroporation of protoplasts and whole cells and tissues have also been described. Saker, M., Kuhne, T., Biologia Plantarum, 40(4):507-514 (1997/98); Donn, et al., In Abstracts of VIIth International Congress on Plant Cell and Tissue Culture IAPTC, A2-38, p. 53 (1990); D'Halluin, et al., Plant Cell, 4:1495-1505 (1992); and Spencer, et al., Plant Mol. Biol., 24:51-61 (1994). See also Chupean, et al., Bio/technology, 7:5, 503-508 (1989).

Following transformation of plant target tissues, expression of the above-described selectable marker transgenes allows for preferential selection of transformed cells, tissues and/or plants, using regeneration and selection methods now well known in the art.

The foregoing methods for transformation would typically be used for producing a transgenic watermelon line. The transgenic watermelon line could then be crossed with another (non-transformed or transformed) line in order to produce a new transgenic watermelon line. Alternatively, a genetic trait that has been engineered into a particular plant cultivar using the foregoing transformation techniques could be introduced into another line using traditional breeding (e.g., backcrossing) techniques that are well known in the plant breeding arts. For example, a backcrossing approach could be used to move an engineered trait from a public, non-elite inbred line into an elite inbred line, or from an inbred line containing a foreign transgene in its genome into an inbred line or lines which do not contain that transgene. As used herein, "crossing" can refer to a simple X by Y cross, or the process of backcrossing, depending on the context.

Gene Conversions.

When the term "watermelon plant" is used in the context of the present invention, this term also includes any gene conversions of that plant or variety. The term "gene converted plant" as used herein refers to those watermelon plants (e.g., diploid watermelon plants) that are developed, for example, by backcrossing, genetic engineering and/or mutation, wherein essentially all of the desired morphological and physiological characteristics of a variety (e.g., small fruit, round fruit, a fruit with a light green (Charleston Gray) skin color, a fruit with a brittle rind, a fruit with yellow flesh; a dark brown mottled seed color, thin (lacy) vines, small leaves with deep lobes, one or more of the disease resistances of SP-7 (e.g., resistance to Anthracnose Race 1, resistance to *Fusarium* Wilt Races 1 and 2 and/or resistance to Powdery Mildew Race 1), earlier presentation of male flowers as compared with cultivar SP-6, production of larger male flowers as compared with cultivar SP-6 and/or production of more male flowers at peak flowering time as compared with SP-6, in any combination) are recovered in addition to the one or more genes transferred into the variety.

To illustrate, backcrossing methods can be used with the present invention to improve or introduce a characteristic into the variety. The term "backcrossing" as used herein refers to the repeated crossing of a hybrid progeny back to the recurrent parent, e.g., backcrossing 1, 2, 3, 4, 5, 6, 7, 8, 9, or more times to the recurrent parent. The parental plant that contributes the gene for the desired characteristic is termed the "nonrecurrent" or "donor parent." This terminology refers to the fact that the nonrecurrent parent is generally used one time in the breeding e.g., backcross) protocol and therefore does not recur. The gene that is transferred can be a native gene, a mutated native gene or a transgene introduced by genetic engineering techniques into the plant (or ancestor thereof). The parental plant into which the gene(s) from the nonrecurrent parent are transferred is known as the "recurrent" parent as it is used for multiple rounds in the backcrossing protocol. Poehlman & Sleper (1994) and Fehr (1993). In a typical backcross protocol, the original variety of interest (recurrent parent) is crossed to a second variety (nonrecurrent parent) that carries the gene(s) of interest to be transferred. The resulting progeny from this cross are then crossed again to the recurrent parent and the process is repeated until a plant is obtained wherein essentially all of the desired morphological and physiological characteristics of the recurrent parent are recovered in the converted plant in addition to the transferred gene(s) and associated trait(s) from the nonrecurrent parent.

Many gene traits have been identified that are not regularly selected in the development of a new line but that can be improved by backcrossing techniques. Gene traits may or may not be transgenic. Examples of these traits include, but are not limited to, male sterility, modified fatty acid metabolism, modified carbohydrate metabolism, herbicide resistance, pest or disease resistance (e.g., resistance to bacterial, fungal, or viral disease), insect resistance, enhanced nutritional quality, increased sweetness, increased flavor, improved ripening control, improved salt tolerance, industrial usage, yield stability, and yield enhancement. These genes are generally inherited through the nucleus.

Genetic Analysis of Watermelon Line SP-7.

The invention further provides a method of determining a genetic characteristic of watermelon line SP-7 or a progeny thereof, e.g., a method of determining a genotype of watermelon line SP-7 or a progeny thereof. In embodiments, the method comprises detecting in the genome of a SP-7 plant, or a progeny plant thereof, at least a first polymorphism (e.g., by detecting a nucleic acid marker by a method comprising nucleic acid amplification and/or nucleic acid sequencing). To illustrate, in embodiments, the method comprises obtaining a sample of nucleic acids from the plant and detecting at least a first polymorphism in the nucleic acid sample. Optionally, the method may comprise detecting a plurality of polymorphisms (e.g., two or more, three or more, four or more, five or more, six or more, eight or more or ten or more polymorphisms, etc.) in the genome of the plant. In representative embodiments, the method further comprises storing the results of the step of detecting the polymorphism(s) on a computer readable medium. The invention further provides a computer readable medium produced by such a method.

The invention will now be described with reference to the following examples. It will be appreciated by those skilled in the art that these examples do not limit the scope of the claims to the invention, but are rather intended to be exemplary of certain embodiments. Other embodiments of the invention may be practiced without departing from the spirit and the scope of the invention, the scope of which is defined by the disclosure and the appended claims.

EXAMPLES

Example 1

Watermelon varieties SP-7 and SP-6 were compared in multiple field trials for flowering time, male flower diameter, and number of male flowers produced.

Flowering time was measured in field trials over two years and two locations as the number of days after transplant when 50% of the plants in each plot presented open male flowers. As shown in FIG. 1, SP-7 (left bars) consistently produced male flowers at an earlier time than SP-6 (right bars). Despite variation in climate during the different seasons, on average, SP-7 presents male flowers approximately seven days earlier than SP-6.

Male flower diameter (cm) was measured at the widest point across fully open male flowers for SP-7 and comparison variety SP-6 over multiple seasons and years in Woodland, Calif. From 2013-2015, flower diameters were recorded in a greenhouse at the Woodland station. In 2016, flower diameters were measured under open field cultivation in a replicated, randomized complete block design. FIG. 2 presents the average male flower diameter recorded for SP-7 (upper line) and SP-6 (lower line). SP-6 had an average male flower diameter of 2.8 cm, and SP-7 had an average of 4.3 cm. These results indicate that SP-7 has consistently larger male flower diameters as compared with SP-6.

To evaluate the number of male flowers produced by SP-7 versus comparison variety SP-6, field experiments were replicated in two locations over multiple seasons and years. Plots of each variety were cultivated in open field conditions with 24" spacing between plants. Male flower number was estimated by counting the number of open male flowers within a square meter of area. For each plot, two measurements were taken on a weekly basis. Peak flowering time was determined as the week when the most open male flowers were recorded across all plots. The results are shown in FIG. 3. Data for SP-7 (left bars) are presented as a percentage of SP-6 (right bars; set at 100%), where % male flower=([SP-7 male flower number]+[SP-6 male flower number])×100. The average percentages for SP-7 are indicated above the bars on the left. As shown, across all years and locations, cultivar SP-7 produced on average 175% more male flowers at peak flowering time than did cultivar SP-6.

Example 2

Triploid watermelon plants are planted in parallel rows 7 feet apart and 3 feet apart within each row. However, plants of watermelon variety SP-7 are planted in a narrow row 3.5' wide (½ the width of the triploid rows) between every second and third triploid row. For example, rows A and B are two consecutive rows of triploids, each 7-foot wide. Row C is a diploid row that is 3.5 feet wide. Row D and E are the following two 7 foot wide rows of triploids, followed by the 3.5-foot wide row F of diploid plants. This pattern is repeated across the width of the field. Because the diploid row is narrower according to the method of the invention, the distance between rows B and D is 10.5 feet instead of a traditional distance of 14 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 3

Triploid watermelon plants are again planted in parallel rows 7 feet apart and 3 feet apart within each row. As in Example 1, plants of watermelon variety SP-7 are planted in a narrow row 3.5' wide, but are planted between every third and fourth triploid row. For example, rows A, B, and C, are three consecutive rows of triploids, each row being 7' wide. The following row D is a diploid row that is 3.5 feet wide. Row E, F, and G are the following three rows of triploids, all 7 feet wide, followed by a 3.5 foot wide row of plants of watermelon variety SP-7. This pattern is repeated across the width of the field. Because the diploid row is narrower according to the method of the invention, the distance between rows B and D is again 10.5 feet instead of a traditional distance of 14 feet. Using this ratio of 1 pollenizer row for every 3 triploid rows (1:3), 25% of the field would normally be used for the pollenizer plants. Reducing the width of the pollenizer row according to the method of the invention by one-half, the gain of space for planting additional triploid plants would be 25%/2 or approximately 12%.

Example 4

Triploid watermelons are planted in parallel rows 8 feet apart and 3 feet apart within each row. Plants of watermelon variety SP-7 are planted in a narrow row 4.0 feet wide (½ the width of the triploid rows) between every second and third triploid row. For example, rows A and B are two consecutive rows of triploids, each 8 foot wide. Row C is a diploid row that is 4.0 feet wide. Row D and E are the following two 8 foot wide rows of triploids, followed by the 4.0 foot wide row F of diploid plants. This pattern is repeated across the width of the field. Because the diploid row is narrower according to the method of the invention, the distance between rows B and D is 12.0 feet instead of a traditional distance of 16 feet. Using this ratio of 1 pollenizer row for every 2 triploid rows (1:2), 33.3% of the field would normally be used for the pollenizer plants. Reducing the width of the pollenizer row according to the method of the invention by one-half, the gain of space for planting additional triploid plants would be 33.3%/2 or approximately 17%.

Example 5

Referring to the above three examples, when triploids are planted in rows 8 feet apart, and the ratio of diploid to triploid is 1:3, it is now clear that the reduction of the pollenizer row width by one-half will gain space for planting additional 12%.

Example 6

It is also within the scope of the invention to reduce the pollenizer row width to approximately ⅓ that of the triploid row width. Thus, according to the present invention, at any row width, when the ratio of diploid rows to triploid rows is:
  (a) 1:2, the savings of field area for additional triploid plants is (33%×⅔) or 22%.
  (b) 1:3, the savings of field area for additional triploid plants is (25%×⅔) or 16.5%.

(c) 1:4, the savings of field area for additional triploid plants is (20%×⅔) or 13.2%.

It is also within the scope of the invention to reduce the pollenizer row width to approximately ⅔ that of the triploid row width.

Example 7

It is also within the scope of the present invention to inter-plant the diploid plants within the rows of triploid plants. According to the invention, the triploid plants are first planted by machine or by hand in regularly spaced rows. The triploid plants within each row are planted, for example, 3 feet apart. After the triploid plants are in the field as described, the diploid pollenizer watermelon plants of the invention are inter-planted, by hand, within each row approximately midway between the triploid plants. When the transplant machine is properly set up, both the triploid plant and pollenizer plant can be transplanted at the same pass. Thus, in this example, the diploid plants are planted approximately 1.5 feet from the flanking triploid plants within the row. Due to the characteristics of watermelon variety SP-7, the diploid plants can be inter-planted within each row after every 2, 3, 4, 5, 6, 7, 8, 9, or 10 consecutive triploid plants. It is currently preferred in the industry to plant the diploid plants after every 2 (1:2) or 3 (1:3) triploid plants within the row. A 1:4 ratio has been reported, but is not normally used in commercial fields due to inadequate pollenization of the triploid plants. The field area saved under this example, when compared with both the current methods of planting diploids in separate rows or within a row at the ratios (diploid:triploid) of:

(a) 1:2, is 33.3%,
(b) 1:3, is 25%,
(c) 1:4, is 20%.

Methods of the present invention comprise planting plants of watermelon variety SP-7 in rows that are narrower than the rows containing the triploid plants. Although the narrower row will encourage growth of plants of watermelon variety SP-7 into the triploid plant row, the characteristics of watermelon variety SP-7 allow it maintain its ability to sufficiently pollinate the triploid plants in the field. Thus, watermelon variety SP-7 and method of the present invention increase the yield of seedless watermelon in a field.

In one aspect, a method of the present invention includes planting a plant of watermelon variety SP-7 within a row of triploid watermelon plants. In one embodiment, a method of the present invention includes planting a plant of watermelon variety SP-7 and a triploid watermelon plant in the same hole. In one embodiment, plants of watermelon variety SP-7 and triploid watermelon plants are planted in a ratio of 3-4:1, i.e. in every 3$^{rd}$ or 4th hole both a plant of watermelon variety SP-7 and a triploid watermelon plant are planted in the same hole. In one embodiment, a plant of watermelon variety SP-7 is planted within pollinating distance of a triploid watermelon plant.

In another aspect, a method of the present invention includes sowing a seed of watermelon variety SP-7 with a seed of triploid watermelon in the same cell of a seedling tray. In one aspect, a method of sowing watermelon seeds is provided, comprising the steps of (1) providing a mechanical seeder; and (2) using said mechanical seeder to seed a seedling tray with triploid seedless watermelon seed and SP-7 watermelon pollenizer seed. In a further aspect, the triploid seedless watermelon seed is planted in each cell of the seedling tray. In another aspect, the SP-7 watermelon pollenizer seed is planted into every 2nd, 3rd or 4th cell of the seedling tray. In another aspect, the ratio of triploid seedless watermelon seeds to SP-7 watermelon pollenizer seeds is 6:1, 5:1, 4:1, 3:1 or 2:1.

Production of Dihaploid Watermelon Plants

Example 8

Anthers of watermelon plants are gamma-ray (produced by cobalt$^{60}$) irradiated for a dose of 0.4 KGy, or 0.3-0.6 KGy of soft X-rays. Irradiated pollen is gently transferred from the anthers to the receptive stigma on or before anthesis. Each ovary of the pollinated female receives an application of 50 ppm CPPU (a plant cytokinin growth regulator) to stimulate fruit development. Plants are monitored for pollination take and fruit development. Fruit is harvested 14 days or 21 days post-pollination.

Harvested immature fruit are carefully cut open under sterile conditions and the seeds are meticulously removed from the flesh. The distal portion of each seed is cut off before plating about 40 seeds to each plate of culture medium. Sealed plates with seeds are cultured at 25° C. with a 16-hour photoperiod in a culture room on a Murashige and Skoog Basal Medium, 30 g/L sucrose, 10 g/L agar supplemented either with 10 µM BA (2.25 mg/L) or 22.2 µM BA (5 mg/L) and 2.85 µM IAA (0.5 mg/L), pH 5.8 and dispensed into 100×15 petri dishes after autoclaving.

After 30 days, seeds are screened for greenish immature embryos for embryo rescue. Those with embryos are moved to fresh medium. As the embryos germinated and elongated, they are transferred to small culture jars with the same medium. When sufficient leaf tissue is present on the plantlet, a leaf is sampled and ploidy analysis is carried out measuring DNA content using flow cytometry (Zhang, Xingping, B. B. Rhodes and J. F. Whitesides, 1994. Determination of watermelon ploidy level using flow cytometry. Cucurbit Genetics Cooperative Rpt 17:102-105), or counting the number of chloroplast in guard cells (N. Sari et al., 1999, Comparison of ploidy level screening methods in watermelon: *Citrullus lanatus* (Thunb.) Matsum. and Nakai-Scientia, Horticulturae 82: 265±277).

Once the plantlets have been confirmed haploid, cuttings/clones are made and rooted in vitro. The medium consists of half strength MS basal salts, 20 g/L sucrose, 1.0 µM IBA (0.2 mg/L), 4 g/L agar and 1 g/L Phytagel, pH 5.8. Once a good root system has developed, plantlets are moved into the greenhouse and planted in trays. The chromosome doubling occurs in the greenhouse by applying 58 µM oryzalin (from product Surflan) to all apical and axillary nodes. Once plants are established and new flowers exhibit the presence of pollen confirming restored fertility, they are self-pollinated and seed is harvested. Further increase can be done in a field isolated from any other watermelon plant, or physically isolated in a net cage. The chromosome doubling process can also be conducted tissue cultures stage (Zhang, Xingping, B. B. Rhodes, H. T. Skorupska and W. Bridges, 1995. Generating tetraploid watermelons using colchicine in vitro. In G. E. Lester and J. R. Dunlap (eds) Cucurbitaceae '94 p 144-147. Gateway Printing, Edinburg, Tex.).

The above examples clearly illustrate the advantages of the invention. Although the present invention has been described with reference to specific details of certain embodiments thereof, it is not intended that such details should be regarded as limitations upon the scope of the claimed invention except as and to the extent that they are included in the accompanying claims.

DEPOSIT INFORMATION

Applicants have made a deposit of at least 2500 seeds of watermelon line SP-7 with the American Type Culture Collection (ATCC), 10801 University Boulevard, Manassas, Va., 20110-2209 U.S.A. under ATCC Deposit No PTA-123747 on Dec. 14, 2016. This deposit of watermelon variety SP-7 will be maintained in the ATCC depository, which is a public depository, for a period of 30 years, or 5 years after the most recent request, or for the effective life of the patent, whichever is longer, and will be replaced if any of the deposited seed becomes nonviable during that period. Additionally, Applicants have satisfied all the requirements of 37 C.F.R. §§1.801-1.809, including providing an indication of the viability of the samples. Access to this deposit will be made available during the pendency of this application to the Commissioner upon request. Upon the issuance of a patent on the variety, the variety will be irrevocably and without restriction released to the public by providing access to the deposit of at least 2500 seeds of the variety with the ATCC. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Variety Protection Act (7 USC §2321 et seq.).

The foregoing invention has been described in detail by way of illustration and example for purposes of clarity and understanding. However, it will be apparent that certain changes and modifications such as single gene modifications and mutations, somaclonal variants, variant individuals selected from large populations of the plants of the instant cultivar and the like may be practiced within the scope of the invention.

What is claimed is:

1. A seed of watermelon cultivar SP-7, wherein representative seed of said cultivar having been deposited under ATCC Accession No. PTA-123747.

2. A plant of watermelon cultivar SP-7, wherein representative seed of said cultivar having been deposited under ATCC Accession No. PTA-123747.

3. A plant part of the plant of claim 2.

4. The plant part of claim 3, wherein the plant part is a fruit, an F1 seed, a shoot, pollen, an ovule, an anther, a root, or a cell.

5. A tissue culture of regenerable cells of the watermelon plant of claim 2.

6. A watermelon plant regenerated from the tissue culture of claim 5 or a selfed progeny thereof, wherein said watermelon plant or selfed progeny thereof comprises all of the physiological and morphological characteristics of watermelon line SP-7.

7. A method of producing watermelon seed, the method comprising crossing the plant of claim 2 with itself or a second watermelon plant and harvesting the resulting seed.

8. An F1 seed produced by the method of claim 7.

9. A watermelon plant, or part thereof, produced by growing the seed of claim 8.

10. A grafted watermelon plant comprising a rootstock and a scion, wherein the plant of claim 2 is used as the rootstock and the scion is from a different watermelon plant.

11. A method of producing a grafted watermelon plant, the method comprising:
(a) providing a rootstock from the plant of claim 2; and
(b) grafting a scion from a different watermelon plant to the rootstock.

12. A method of developing a watermelon line in a watermelon plant breeding program using plant breeding techniques, which include employing a watermelon plant, or its parts, as a source of plant breeding material, comprising:

(a) obtaining the watermelon plant, or its parts, of claim 2 as a source of breeding material; and
(b) applying plant breeding techniques.

13. A method for producing a seed of a watermelon plant derived from the watermelon cultivar SP-7, the method comprising:
(a) crossing the plant claim 2 with a different watermelon plant; and
(b) allowing seed to form;
(c) growing a plant from the seed of step (b) to produce a plant derived from watermelon cultivar SP-7;
(d) self ing the plant of step (c) or crossing it to a second watermelon plant to form additional watermelon seed derived from watermelon cultivar SP-7; and
(e) optionally repeating steps (c) and (d) one or more times to generate further derived watermelon seed from watermelon cultivar SP-7, wherein in step (c) a plant is grown from the additional watermelon seed of step (d) in place of growing a plant from the seed of step (b).

14. A method of vegetatively propagating watermelon cultivar SP-7, the method comprising:
(a) collecting tissue capable of being propagated from the plant of claim 2;
(b) cultivating the tissue to obtain proliferated shoots;
(c) rooting the proliferated shoots to obtain rooted plantlets; and
(d) optionally, growing plants from the rooted plantlets.

15. A watermelon plantlet or plant obtained by the method of claim 14, wherein the watermelon plantlet or plant comprises all of the physiological and morphological characteristics of watermelon cultivar SP-7.

16. A method of introducing a desired added trait into watermelon cultivar SP-7, the method comprising:
(a) crossing the plant of claim 2 with a watermelon plant that comprises a desired added trait to produce F1 progeny;
(b) selecting an F1 progeny that comprises the desired added trait;
(c) crossing the selected F1 progeny with watermelon cultivar SP-7 to produce backcross progeny;
(d) selecting a backcross progeny comprising the desired added trait and; and
(e) optionally repeating steps (c) and (d) one or more times to produce a plant derived from watermelon cultivar SP-7 comprising a desired added trait and essentially all of the physiological and morphological characteristics of watermelon cultivar SP-7, wherein in step (c) the selected backcross progeny produced in step (d) is used in place of the selected F1 progeny of step (b).

17. A watermelon plant produced by the method of claim 16 or a selfed progeny thereof, wherein the watermelon plant or selfed progeny thereof has the desired added trait.

18. Seed that produces the plant of claim 17.

19. A method of producing a plant of watermelon cultivar SP-7 comprising a desired added trait, the method comprising introducing a transgene conferring the desired trait into the plant of claim 2.

20. A watermelon plant produced by the method of claim 19 or a selfed progeny thereof, wherein the watermelon plant or selfed progeny thereof comprises the transgene and has the desired added trait and otherwise has all of the physiological and morphological characteristics of watermelon cultivar SP-7.

21. Seed that produces the plant of claim 20.

22. A method of producing triploid, seedless watermelon fruit, wherein the method comprises:

(a) interplanting a diploid watermelon plant according to claim 2 and a triploid watermelon plant; and
(b) allowing pollination of the triploid watermelon plant by pollen of the diploid watermelon plant to obtain triploid, seedless watermelon fruit.

23. The method according to claim 22, wherein the method further comprises harvesting the triploid, seedless watermelon fruit.

24. The method according to claim 22, wherein the step of interplanting the diploid watermelon plant and the triploid watermelon plant comprises planting seed to produce the diploid watermelon plant and/or the triploid watermelon plant.

25. The method according to claim 22, wherein the step of interplanting the diploid watermelon plant and the triploid watermelon plant comprises planting a diploid watermelon transplant and/or a triploid watermelon transplant.

26. A triploid, seedless watermelon fruit produced by the method according to claim 22.

27. A method of sowing watermelons seeds, the method comprising:
(a) providing a mechanical seeder; and
(b) using the mechanical seeder to seed a seeding tray with (i) the seed of claim 1, and (ii) triploid watermelon seed.

* * * * *